(12) United States Patent
Veyrent et al.

(10) Patent No.: US 11,097,053 B2
(45) Date of Patent: Aug. 24, 2021

(54) AUTOMATIC INJECTION OF MEDICATION INTO ANIMALS

(71) Applicant: DESVAC, Saint Barthelemy d'Anjou (FR)

(72) Inventors: Stephane Veyrent, Soulaines sur Aubance (FR); Erwan Fonteny, Angers (FR); Julie Mars, Maze (FR)

(73) Assignee: DESVAC, Saint Barthelemy d'Anjou (FR)

( * ) Notice: Subject to any disclaimer, the term of this patent is extended or adjusted under 35 U.S.C. 154(b) by 92 days.

(21) Appl. No.: 16/375,532

(22) Filed: Apr. 4, 2019

(65) Prior Publication Data

US 2019/0290847 A1  Sep. 26, 2019

Related U.S. Application Data

(63) Continuation of application No. 15/540,391, filed as application No. PCT/IB2015/060035 on Dec. 29, 2015, now abandoned, which is a continuation of application No. 14/584,690, filed on Dec. 29, 2014, now abandoned.

(51) Int. Cl.
*A61M 5/20* (2006.01)
*A61D 7/00* (2006.01)

(52) U.S. Cl.
CPC ............... *A61M 5/20* (2013.01); *A61D 7/00* (2013.01); *A61M 5/2033* (2013.01); *A61M 2005/206* (2013.01); *A61M 2005/2013* (2013.01)

(58) Field of Classification Search
CPC .............. A61M 5/20; A61M 5/2033; A61M 2005/2013

(Continued)

(56) References Cited

U.S. PATENT DOCUMENTS 5,961,494 A * 10/1999 Hogan ................... A01K 11/00
604/191
2002/0133113 A1  9/2002 Madsen et al.
(Continued)

FOREIGN PATENT DOCUMENTS

CN         103945880 A    7/2014
EP         1 728 529 B1   7/2008
(Continued)

OTHER PUBLICATIONS

Russian Office Action dated May 27, 2020 in Russian Patent Application No. 2020111411 (with English translation), 6 pages.
(Continued)

*Primary Examiner* — Phillip A Gray
(74) *Attorney, Agent, or Firm* — Oblon, McClelland, Maier & Neustadt, L.L.P.

(57) ABSTRACT

In selected embodiments, a handheld injection safety applicator includes an applicator housing with a handle and a retractable needle housed within the applicator. The applicator further includes a first sensor that detects the presence of a user's grip on the handle and a second sensor that detects the presence of an animal. The applicator also includes processing circuitry configured to receive a first signal from the first sensor indicating that the user is gripping the handle and receive a second signal from the second sensor indicating that an animal is detected. The applicator extends the needle out of the applicator into the animal once the first and second signal are received and delivers a dose of medication into the animal once the needle is fully extended into the animal.

15 Claims, 21 Drawing Sheets

(58) Field of Classification Search
USPC .......................................................... 604/503
See application file for complete search history.

(56) References Cited

U.S. PATENT DOCUMENTS

| | | | |
|---|---|---|---|
| 2009/0131875 A1* | 5/2009 | Green | A61M 5/178 604/187 |
| 2012/0071818 A1 | 3/2012 | Lauchard et al. | |
| 2013/0131595 A1* | 5/2013 | Ekman | A61M 5/1452 604/117 |
| 2014/0207106 A1 | 7/2014 | Bechmann et al. | |
| 2014/0221974 A1 | 8/2014 | Bechmann et al. | |
| 2014/0257185 A1 | 9/2014 | Bechmann et al. | |
| 2016/0001005 A1 | 1/2016 | Bechmann et al. | |
| 2016/0038266 A1 | 2/2016 | Edwards | |

FOREIGN PATENT DOCUMENTS

| | | |
|---|---|---|
| WO | WO 2006/134153 A1 | 12/2006 |
| WO | WO 2013/034984 A2 | 3/2013 |
| WO | WO 2013/034984 A3 | 3/2013 |
| WO | WO 2014/107766 A1 | 7/2014 |

OTHER PUBLICATIONS

Combined Chinese Office Action and Search Report dated Apr. 27, 2020, in Patent Application No. 201580077157.7, 25 pages (with English translation).
European Office Action dated Jan. 3, 2020 in Patent Application No. 15 823 820.4, 4 pages.
Office Action dated Jun. 18, 2019 in corresponding Russian Patent Application No. 2017126992 (with English Translation), 10 pages.
Brazilian Office Action dated Dec. 29, 2015, in Patent Application No. BR112017013900-6, 5 pages (with English translation).
Combined Chinese Office Action and Search Report dated Sep. 3, 2019, in Patent Application No. 201580077157.7 (with English translation), 23 pages.
Combined Russian Office Action and Search Report dated Oct. 11, 2019, in Patent Application No. 2017126992, 17 pages (with English translation).
International Search Report dated Apr. 15, 2016, in PCT/IB2015/060035, filed Dec. 29, 2015.
Third Office Action dated Dec. 31, 2020 in corresponding Chinese Patent Application No. 201580077157.7 (with English translation) (19 pages).

* cited by examiner

AUTOMATIC INJECTION OF MEDICATION INTO ANIMALS

CROSS-REFERENCE TO RELATED APPLICATIONS

This application is a continuation of and is based upon and claims the benefit of priority under 35 U.S.C. § 120 for U.S. Ser. No. 15/540,391 filed Jun. 28, 2017, which is a 371 continuation of PCT/IB2015/060035 filed Dec. 29, 2015, which is a continuation of U.S. Ser. No. 14/584,690 filed Dec. 29, 2014, and the entire contents of each of the above applications are hereby incorporated herein by reference in entirety.

BACKGROUND

Field of the Invention

The present disclosure relates to applicators, and in particular, but not exclusively, to applicators used to inject medications into animals, such as pigs, for example.

Description of the Related Art

Injections of medication are typically carried out using needle containing injectors or applicators. The term medication is used herein to include any drug, medicine, remedy, therapeutic preparation, vitamins, neutraceuticals, vaccines, antibodies, and the like. These types of applicators are frequently used with animals, especially livestock, because of the large number of animals that need to be injected. Because of the use of needles to administer medications, there is a possibility that the users could accidently stab themselves with the needle, or even inject the medication into themselves.

Injections of medications for livestock can require the user to inject hundreds of animal in a single setting. Each injection requires the user to apply force to insert the needle into each animal and deliver the medication. By injecting hundreds of animals, the user may be subject to repetitive motion injuries.

SUMMARY

In selected embodiments, a handheld injection safety applicator includes an applicator housing with a handle and a retractable needle housed within the applicator. The applicator further includes a first sensor that detects the presence of a user's grip on the handle and a second sensor that detects the presence of an animal. The applicator also includes processing circuitry configured to receive a first signal from the first sensor indicating that the user is gripping the handle and receive a second signal from the second sensor indicating that an animal is detected. The applicator extends the needle out of the applicator into the animal once the first and second signal are received and delivers a dose of medication into the animal once the needle is fully extended into the animal.

In this manner, the retractable needle only extends when the applicator detects that the user is holding the handle and detects the presence of the animal. Because the needle only extends after both sensors have been triggered, accidental needle sticks are minimized, helping make the applicator safer for the user.

The force needed to insert the needle into the animal, and deliver the dose can be provided by a linear actuator within the applicator. Since the insertion of the needle and the delivery of the medication are fully automatic, the process requires little force on the part of the user and the repetitive force and motion of injecting lots of animals is reduced for the user. This may ameliorate problems with repetitive motion injuries and the like.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1A:
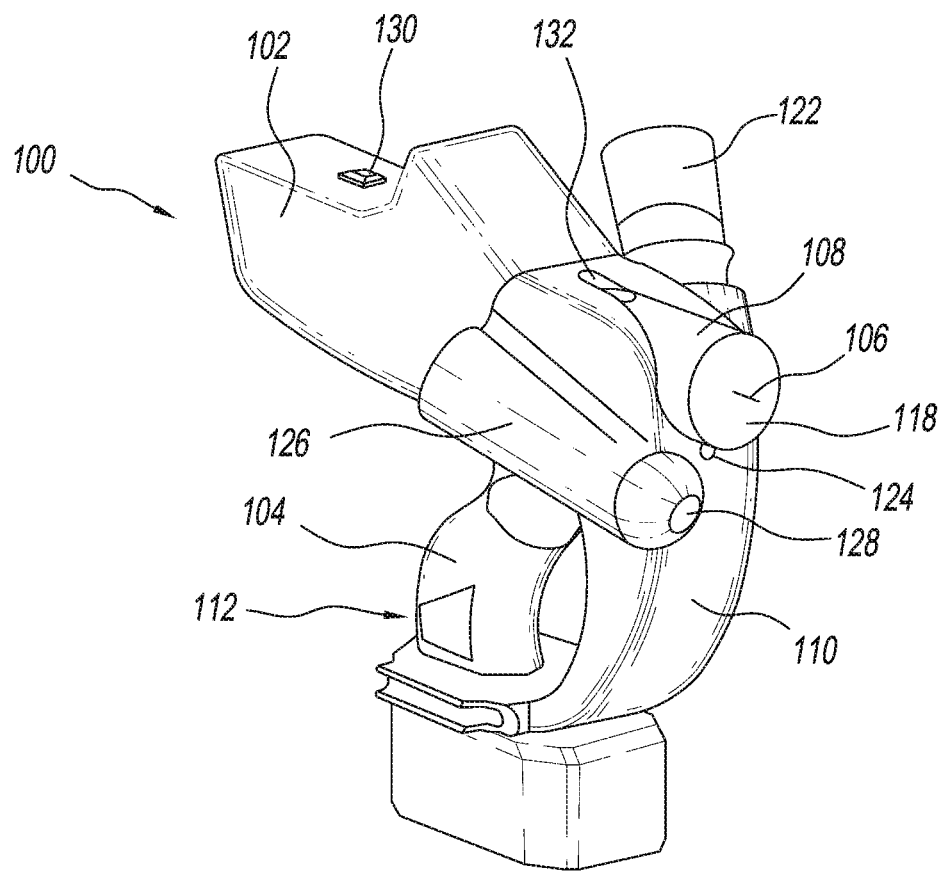
FIG. 1A illustrates an isometric view of an exemplary embodiment of an applicator.

A more complete appreciation of the present advancements and many of the attendant advantages thereof will be readily obtained as the same becomes better understood by reference to the following detailed description when considered in connection with the accompanying drawings. However, the accompanying drawings and their exemplary depictions do not in any way limit the scope of the advancements embraced by the specification. The scope of the advancements embraced by the specification and drawings are defined by the words of the accompanying claims.

Selected embodiments are now described by referring to the drawings, wherein like reference numerals designate identical or corresponding parts throughout the several views. It is noted that, as used in the specification and the appending claims, the singular forms "a," "an," and "the" can include plural references unless the context clearly dictates otherwise.

Figure 1B:
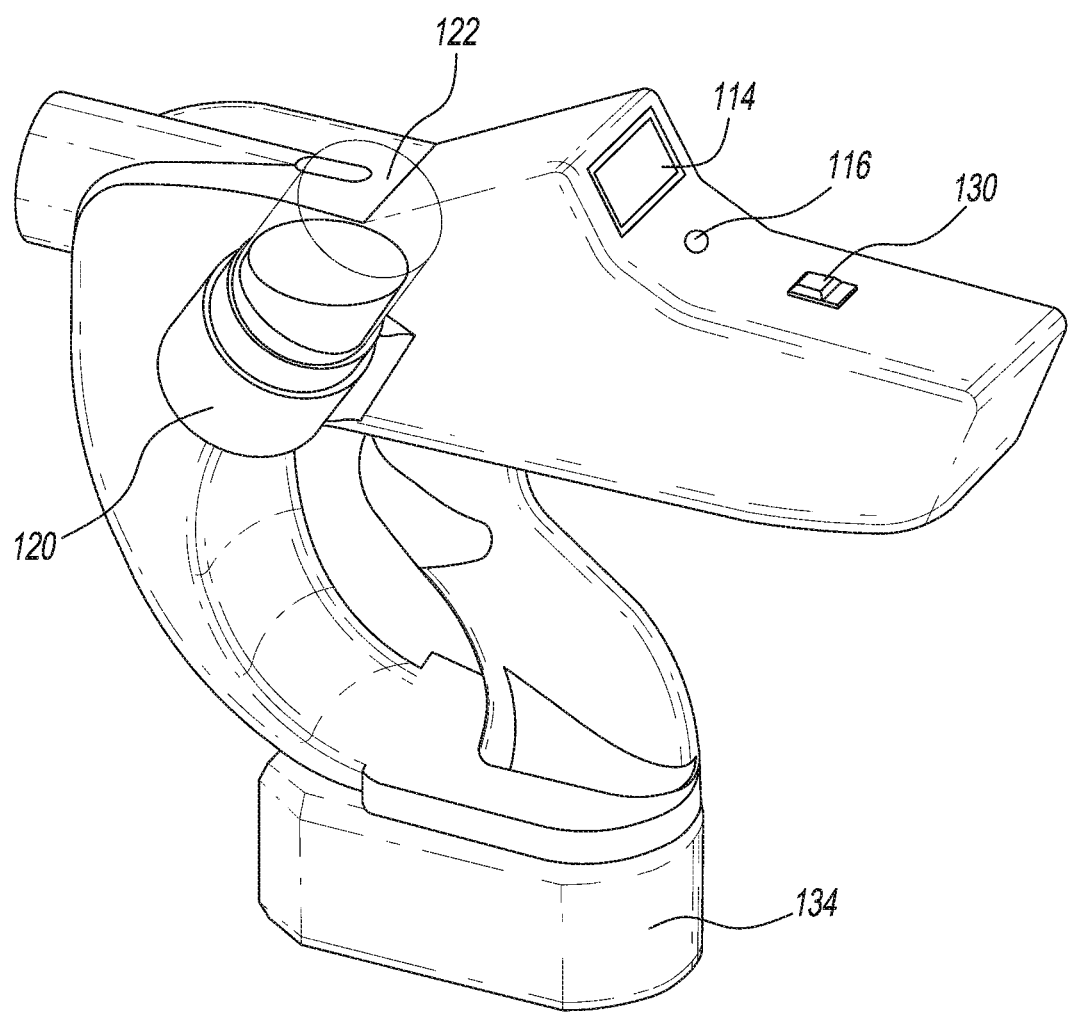
FIG. 1B illustrates an isometric view of the exemplary embodiment of the applicator as shown in FIG. 1A.

Referring to FIGS. 1A-1B, an applicator 100 is illustrated according to an exemplary embodiment of the present disclosure. The applicator 100 can inject medication into animals, for example, livestock. Various types of medication can be injected, for example, drugs, medicines, remedies, therapeutic preparations, vitamins, neutraceuticals, vaccines, antibodies, and the like. The applicator 100 can be used to inject various animals, such as cattle, pigs, horses, poultry, goats, sheep, cats, dogs, and the like.

According to an exemplary embodiment, the applicator 100 provides a safe, handheld, fully automatic repeater medication apparatus for dispensing a predetermined volume of a fluid, such as a vaccine, into an animal, such as a pig, and reloading the applicator 100 after each volume of liquid is dispensed.

The applicator 100 is typically a handheld device. The applicator includes an applicator housing 102, a handle 104, and a retractable needle 106. Within the housing 102, an insertion and delivery mechanism is configured to extend the needle 106 out of the applicator 100 and insert the needle 106 into an animal and deliver a predetermined amount of medication.

After the animal is injected, the needle 106 retracts backs into the housing 102, and a new dose is loaded. The needle 106 is housed in a nose 108 of the applicator 100. By keeping the needle retracted at all times, expect for during the injection process, accidental needle sticks can be minimized. The retractable needle 106 can be replaced after several injections to maintain the integrity of the retractable needle 106.

The applicator 100 may include a hand guard 110 that is placed in front of the handle 104, to act as a guard between the handle 104 and the animal being injected.

In an exemplary embodiment, the handle 104 does not include a mechanical trigger for injection, and does not include any manual mechanism for actively activating the injection. The insertion of the needle 106 into the animal, and the delivery of the medication are done automatically, as described next. This can be accomplished through the use of sensors on the applicator 100. When the sensors detect a particular situation, the applicator 100 inserts the needle 106 into the animal, and delivers the dose, with minimal action from the user.

For example, the applicator 100 can have two different sensors. A first sensor that detects the user's presence and a second sensor that detects the presence of the animal.

Figure 1C:
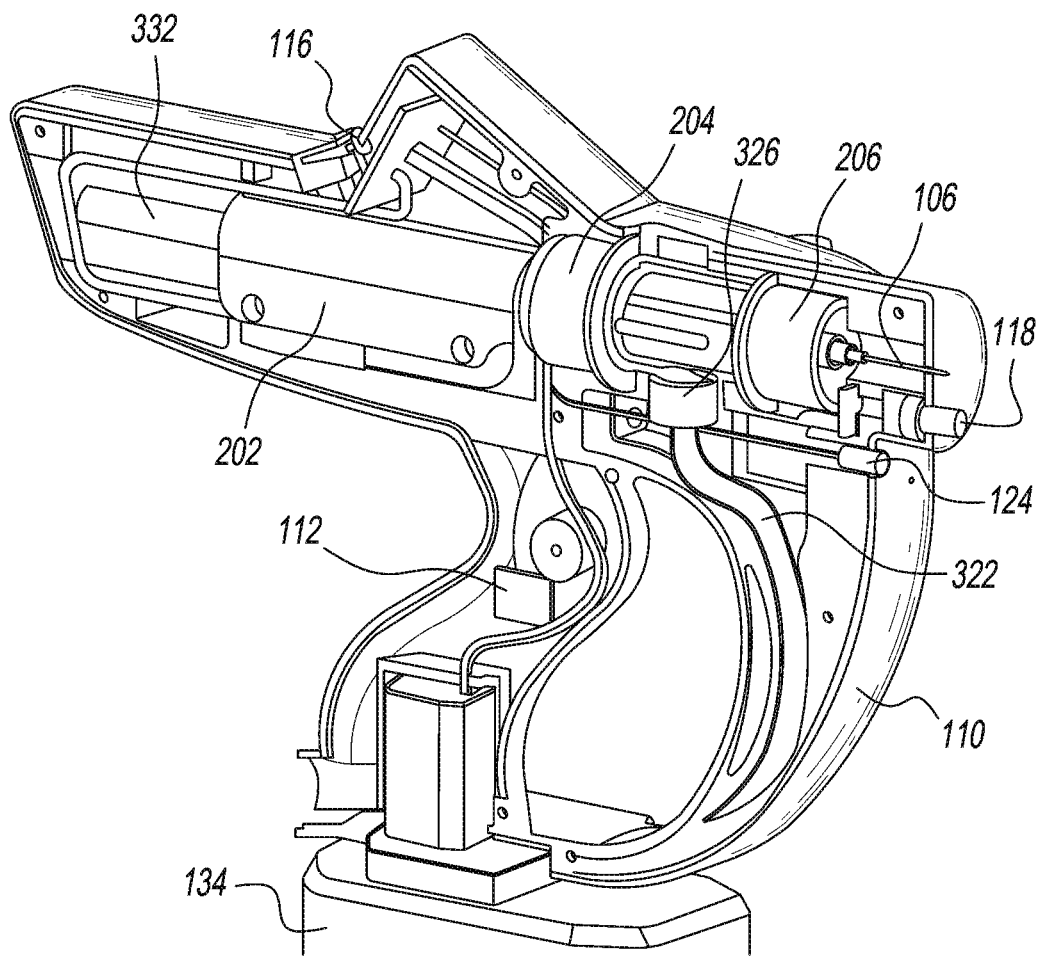
FIG. 1C illustrates an isometric cross-sectional view of an exemplary embodiment of the applicator of FIG. 1A.

For example, the first sensor can be a handle presence sensor 112 that senses the user gripping the handle 104. Therefore, when the user grabs the handle 104 of the applicator 100 with their hand, the handle presence sensor 112 is activated. The handle presence sensor 112 can be a capacitive sensor that uses a thin copper sheet placed inside the handle as illustrated in FIG. 1C, or any type of sensor for detecting the user's presence known to one skilled in the art. The handle presence sensor 112 sends a signal to processing circuitry to turn on the applicator 100 and to prepare for injection. When the applicator is turned on, a screen 114 and a light 116 turn on and light up to indicate to the user that applicator 100 is ready for use.

The screen 114 may display useful information to the user about the applicator 100. For example, the screen 114 may display the status for the applicator, the number of injections performed, the approximate number of injections that can be performed with the remaining medication bottle, etc. The screen 114 can also display error codes or warnings to inform the user of any problems or potential problems, such as low battery, loss of sensor reading, scheduled maintenance, etc.

The light 116 can be an LED, and the light 116 can indicate to the user when the applicator is turned on. The LED 116 can also indicate when the applicator 100 is ready to vaccinate, when the vaccination is in process, when an error occurs, etc. Different colors, blinking lights, and different light sequences can inform the user of different scenarios. Alternatively, or in addition, the applicator 100 can include other sensory indicators, such as a sound or vocal indicator.

The second sensor can be an animal contact sensor 118, such as a LDC1051 of Texas Instruments. An example of a mechanical animal contact sensor 118 is illustrated in FIG. 1C. The animal contact sensor can include a solid member that is parallel to the retractable needle 106. When the solid member comes in contact with the animal skin, the solid member retracts from an extended position to a retracted position. When the solid member is in a retracted position, a signal is sent to the processing circuitry that the nose 108 of the applicator 100 is against the skin of the animal. For example, when the user places the nose 108 of the applicator 100 in contact with the skin of the animal, the solid member depresses which indicates that the user is applying the nose 108 of the applicator 100 on the animal. Various sensors are within the scope of the present description, including non-contact sensors, magnetic sensors, electrical sensors, mechanical sensors, optical sensors and the like.

When both sensors send the appropriate signal to the processing circuitry, the processing circuitry controlled applicator 100 can control the extension of the needle 106. After the needle 106 is fully extended, the processing circuitry can control the administration of a dose of medication to the animal automatically and without any further action from the user. In an exemplary embodiment the needle 106 cannot extend without the processing circuitry receiving a signal from both sensors. A linear actuator within the applicator can apply the force needed to insert the needle 106 into the animal and deliver the dose.

The extension of the needle 106 from the applicator 100 and insertion into the animal can be regulated to ensure that the proper depth of the needle 106 is achieved to properly administer the dose. Because the needle 106 is inserted to a proper distance, an exact dose can be administered. In settings where large amounts of animals are injected, sometimes a proper amount of medication is not injected into the animal, leaving an animal undermedicated for its intended purpose. To compensate for undermedicating an animal, some users administer a large dose of medication to ensure that every animal receives enough medication. However, this practice wastes medication by overmedicating most of the animals. By ensuring that the exact dose is administered, the animals do not need to receive larger doses to ensure that all the animals receive the proper amount. This way, medication is conserved.

The applicator 100 can also include a medication slot 120. The medication slot 120 can be located on one of the sides of the applicator 100. A medication bottle 122 can be inserted into medication slot 120. Once the medication bottle 122 is inserted in the medication slot 120, the medication bottle 122 acts as a medication reservoir for storing the medication. After each injection, a predetermined amount of medication is pumped from the medication bottle 122 into the applicator 100 for the next dose. The size of the medication bottle 122 and the volume of medication it holds can vary.

In another embodiment, the medication may be housed off the applicator 100. For example, the user can carry a medication bag with tubing that would connect to the applicator 100 to provide medication to the applicator 100.

In an exemplary embodiment, the applicator can also include a guiding mechanism 124. For example, a laser or LED can be used to help guide the user. The guiding mechanism 124 can be located near the needle exit. The processing circuitry can control the operation of the laser 124, which can be turned on when the processing circuitry has determined that the user is gripping the handle 104, there is medication in the applicator 100, and there is enough battery power. The user can focus the laser on a specific location on an animal to inject the medication. This can help ensure the user inserts the needle 106 in the proper location on the animal.

In another embodiment, the applicator 100 can have a second slot 126 on the opposite side of the medication slot 120. The second slot 126 can house marker ink for marking the animal after the animal has been injected with a dose of medication. The second slot 126 can have an orifice 128 through which the ink can be actuated to mark the animal. Improperly marking an animal before it has received a dose can lead to the user believing that animal has received a dose when it actually has not. Or if the animal does not receive enough medication, the animal may not be properly medicated. Therefore, the processing circuitry can control the delivery of the ink, such that the ink only marks the animal after a successful delivery of the medication has been performed.

The applicator 100 can further include a reset button 130. The reset button 130 can be used to reset any error messages on the LED 116. The reset button 130 can also be used to set or reset the vaccination counter.

The reset button 130 can also be used to initiate a Clean In Place (CIP) process, that is used to clean the internal components of the applicator, especially a cavity that holds the medication. The medication bottle is replaced with a water bottle and the internal cavity is cleaned.

The applicator 100 can further include a window 132 in the applicator housing 102. The window 132 allows the user to look inside the housing 102 of the applicator 100 and see the cavity that houses the medication inside the applicator 100. The window 132 may be placed on the top of the housing 102, but it can be placed in different locations on the applicator housing 102.

The applicator 100 can further include a battery pack 134. The battery pack 134 provides power to run the processing circuitry within the applicator 100 and power the linear actuator. The battery pack 134 may be a standard 18V rechargeable battery pack that is commercially available, such as a Ryobi 18 volt lithium-ion rechargeable battery. The battery pack 134 can also have a battery sensor for detecting the energy level of the battery and send a signal to the processing circuitry if the battery is low. The processing circuitry can inform the user of the low battery.

Figure 2:
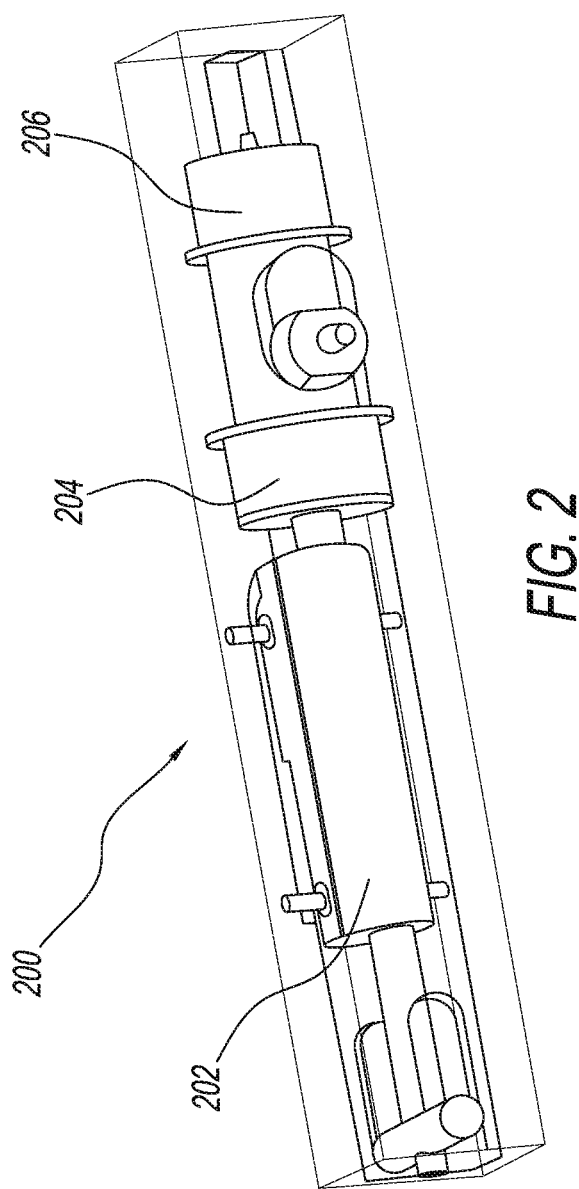
FIG. 2 illustrates an isometric view of a two stage insertion and delivery mechanism that is within the housing of the applicator according to an exemplary embodiment.

FIG. 1C illustrates an isometric cross-sectional view of the applicator 100, and shows the internal components of the applicator 100. FIGS. 1C and 2 illustrate an exemplary embodiment of the insertion and delivery mechanism 200. The insertion and delivery mechanism 200 provides a two stage injection process. The insertion and delivery mechanism 200, and the two stage injection process can be controlled by the processing circuitry. In the first stage, the animal is inserted with the needle 106. In the second stage, the medication is delivered to the animal through the needle 106. The insertion and delivery mechanism 200 is driven by a linear actuator 202, which applies the force needed to extend the needle 106 out of the applicator 100 and insert the needle 106 into the animal, and also deliver the dose of medication through an orifice 312 of the needle 106 into the animal.

FIG. 2 further illustrates a pair of bearings, a first bearing 204 and a second bearing 206, which house a portion of the insertion and delivery mechanism 200. In the following discussion, the term proximal refers to the portion of the applicator 100 nearest to the user, or the back of the applicator 100 and distal refers to the nose 108 of the applicator or closer to the needle 106.

Figure 3:
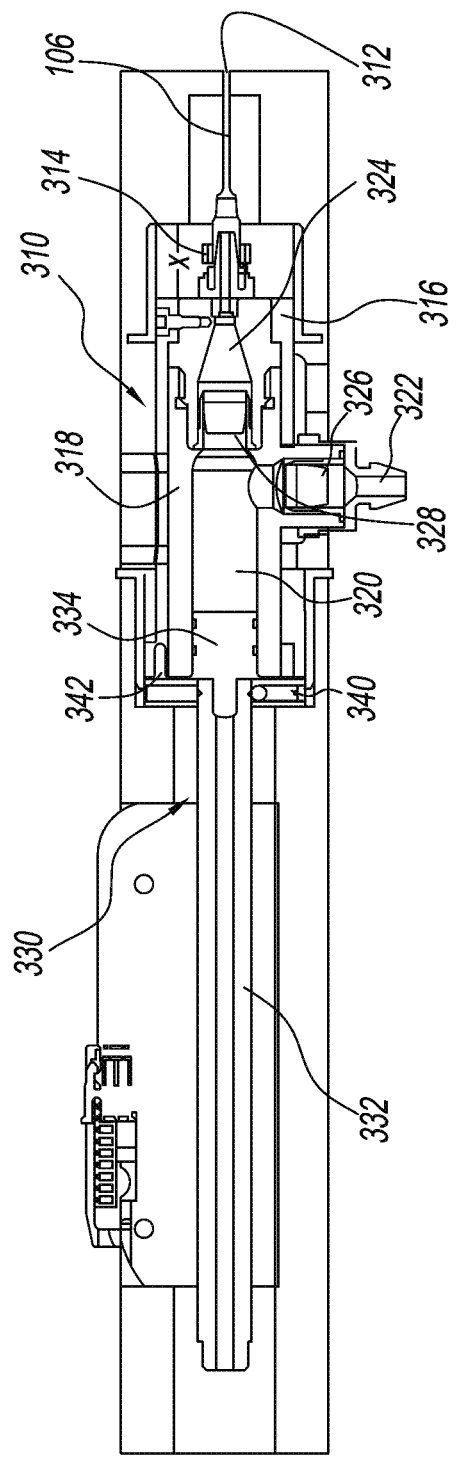
FIG. 3 illustrate a cross-sectional view of the two stage insertion and delivery mechanism according to the exemplary embodiment of FIG. 2.

FIG. 3 illustrates in greater detail an exemplary embodiment of the insertion and delivery mechanism 200. The insertion and delivery mechanism 200 facilitates the two stage insertion of the needle 106 and medication delivery process. The insertion and delivery mechanism 200 includes an insertion portion 310 and a delivery portion 330.

Figure 4:
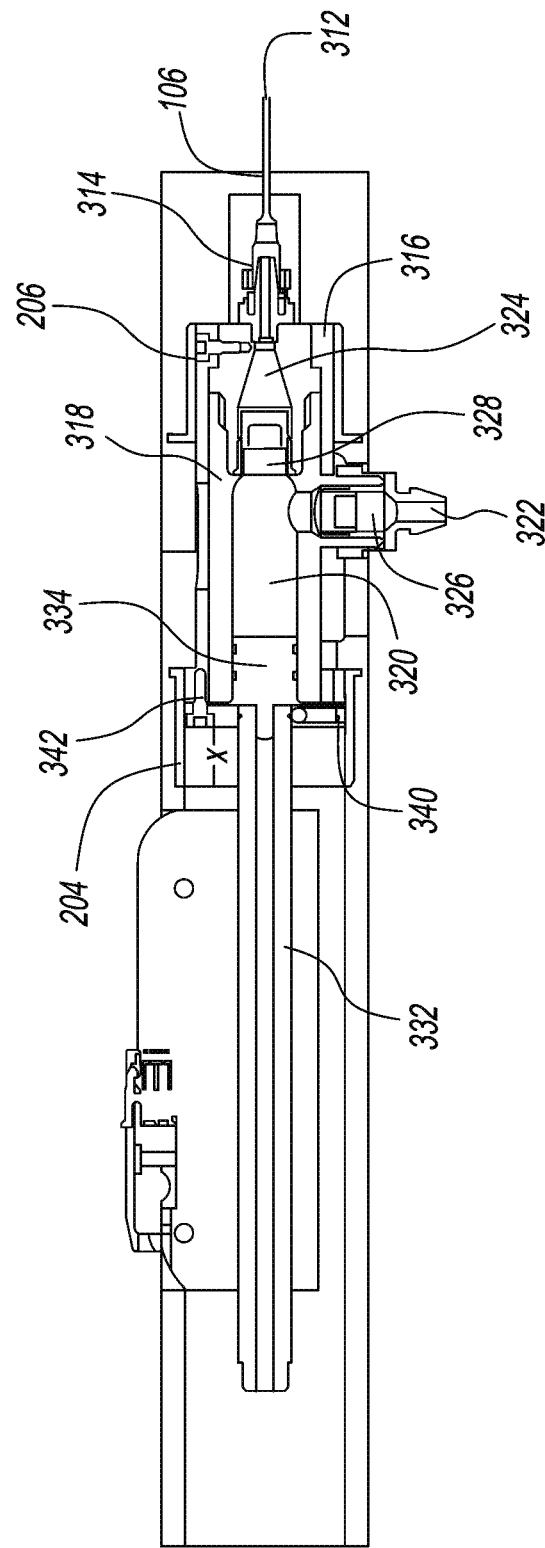
FIG. 4 illustrates a cross-sectional view of the two stage insertion and delivery mechanism during a first stage according to the exemplary embodiment of FIG. 2.

In the first stage, the insertion portion 310 and the delivery portion 330 move together a distance "x," and the needle 106 extends out of the applicator 100, and inserts into the skin of the animal. This extension is illustrated in FIG. 4. The amount of force applied by the linear actuator 202 is dependent upon the amount of force needed to push the needle 106 into the animal. In an exemplary embodiment, the amount of force needed to insert the needle 106 into the animal is 5N±1N. However, the amount of force required to insert the needle 106 into the animal is dependent on a number of factors, such as the size of the needle 106, the type of animal, the size of the animal, the speed of the insertion, etc.

Figure 5:
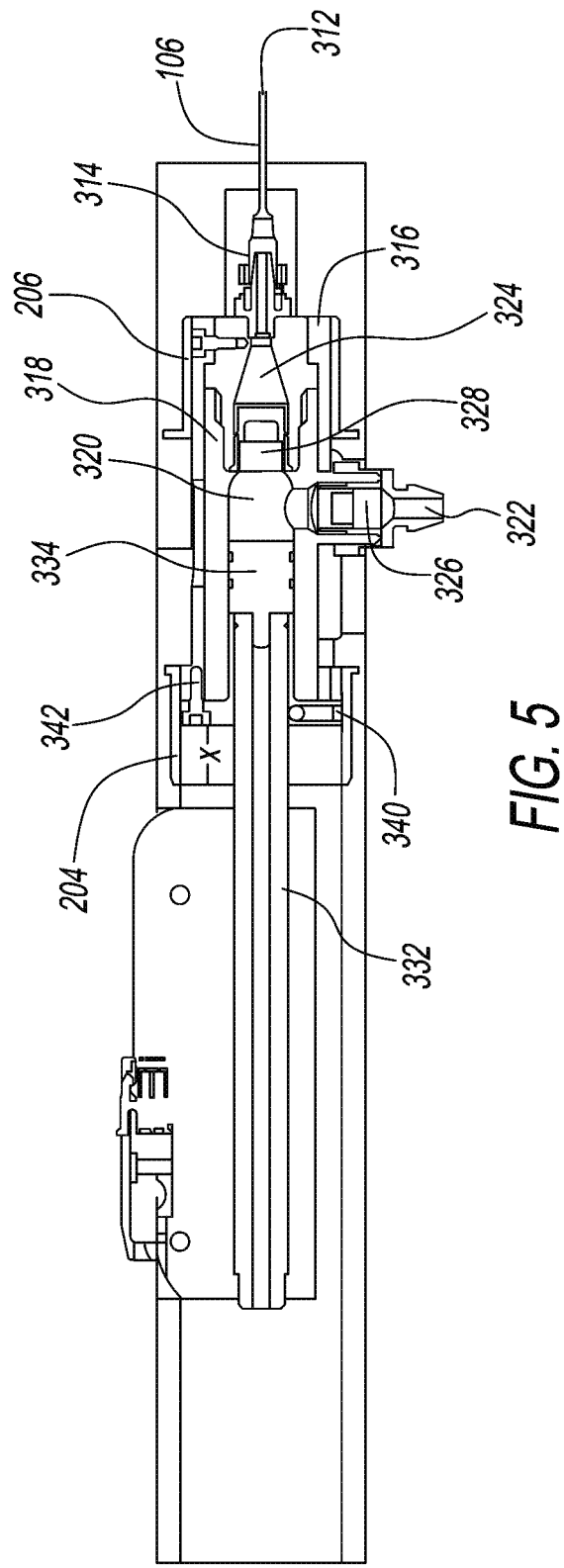
FIG. 5 illustrates a cross-sectional view of the two stage insertion and delivery mechanism during a second stage according to the exemplary embodiment of FIG. 2.

In the second stage, the delivery portion 330 moves independently of and within the insertion portion 310 and subsequent to the insertion of the needle 106 into the animal. The independent movement of the delivery portion 330 allows the delivery of the medication through the needle 106 to the animal. This second stage is illustrated in FIG. 5. The amount of force applied by the linear actuator 202 is dependent upon the amount of force needed to deliver the medication through the orifice 312 of the needle 106 into the animal. In an exemplary embodiment, the amount of force needed to deliver a specific vaccine into the animal is 65N±5N. However, the amount of force required to deliver the medication into the animal is dependent on a number of factors, such as the viscosity of the medication, the size of the needle, the size of the orifice in the needle, the speed of the delivery, the size of the dose, the size of a piston, the type of animal being injected etc.

The insertion portion 310 may include the needle 106, a needle support 314, a syringe block 316, a syringe cavity or chamber block 318, a syringe cavity or chamber 320, an inlet 322, and an outlet 324. The insertion portion 310 of the insertion and delivery mechanism 200 is housed between the first bearing 204 and the second bearing 206.

The structure of the insertion portion 310 can be explained through the process of the insertion of the needle 106 into the animal and the delivery of the medication. The cavity 320 stores a single dose of medication, such as a vaccine to administer. The size of the dose is predetermined, but a typical dose may be 2 ml. The size of the dose may vary, depending on the medication being given, the animal being administer, the size of the animal, etc.

The dose enters the cavity 320 from an external source, through an inlet 322, by way of a check valve 326 such as a duckbill valve. This ensures that the medication does not pass back to the external source after passing through the check valve 326. The external source of medication may be the medication bottle 122 that is inserted in the medication slot 120 on the outside of the applicator 100 or a medication bag that is connected to the applicator 100 by tubing. When a predetermined amount of force is applied to the dose in the cavity, the dose exits through the second check valve 328, and passes through the outlet 324 and eventually passes through the orifice 312 of the needle 106 and into the animal.

The needle 106 is supported by the needle support 314, which adds stability to the needle 106. The needle support 314 is attached to the cavity block 318. The outlet 324 that the medication passes through from the cavity 318 to the needle 106 is found in the needle support 314 after the second check valve 328.

The cavity block 318 and a majority of the needle support 314 are found within the syringe block 316. The syringe block 316 spans a majority of the length from the first bearing 204 to the second bearing 206. In the off state, or in its unactuated state, the proximal end of the syringe block 316 is near the proximal end of the first bearing 204. There is a gap "x" between the distal end of the syringe block 316 and the distal end of the second bearing 206. The syringe block 316 may be actuated and moved a distance "x" between the first bearing 204 and the second bearing 206. The distance "x" can be 16 mm±2 mm. The bearings 204 and 206 may be self-lubricating which may allow the syringe block 316 to be moved more easily between the two bearings 204 and 206.

In another exemplary embodiment, the insertion portion 310 can further include a heater to heat up the medication to make the medication less vicious.

The delivery portion 330 includes a rod 332 and a piston 334. The piston 334 is attached to the distal end of the rod 332, but the piston is detachable. The linear actuator 202 provides axial movement of the rod 332 and the piston 334, which provides the force need to insert the needle 106 and deliver the medication. The processing circuitry determines the amount of force the linear actuator 202 applies by the axial movement of the rod 332 or the distance the rod 332 travels.

The cavity 320 found within the cavity block 318 opens at the proximal end of the cavity block 318. This opening allows the piston 334 to fit within the cavity 320. The cavity 320 may be cylindrical with a circular cross section. A diameter of the piston 334 is slightly smaller than a diameter of the cavity 320 to allow the piston 334 to move within the cavity 320.

The piston 334 may further includes a plurality of seals 336 that wrap circumferentially around the piston 334 in order to seal the cavity 320 from the open end of the cavity block 318 when the piston 334 is within the cavity 320.

In another embodiment, there can be an internal medication sensor that detects the presence of the medication in the cavity 320. The medication sensor transmits a signal to the processing circuitry to indicate that there is medication in cavity 320. If there is no medication in the cavity 320, a signal is sent to the processing circuitry, which prevents the actuation of the applicator 100.

In another embodiment, the volume of the cavity 320 can be varied by the changing the initial placement of the piston 334 inside the cavity 320. The initial placement of the piston 334 can be customized by the user, and controlled by the processing circuitry, thereby allowing the user to adjust the amount of vaccine administered to the animal.

In another embodiment, the applicator can have a latch that locks the injection portion 310 of the applicator 100 in place. Therefore, the delivery portion 330 can move independently of the insertion portion 310. The latch can be switched between a locked position and an unlocked position by the processing circuitry. The applicator 100 can further include a latch sensor to determine whether the latch is in the locked or unlocked position.

The applicator 100 can be primed before use to help remove air bubbles from the vaccine and for more accurate dosage. When a new medication bottle is inserted into the applicator 100, the applicator 100 is primed by the user activating the latch, which locks the insertion portion 310 in place. With the insertion portion 310 locked, the delivery portion 330 can move independently and the user can run one delivery process independent of the insertion portion 310. This will prime the cavity and remove air bubbles from the cavity 320.

The user can also activate the latch to perform CIP. The user activates the latch to prevent the movement of the injection portion 310. The user can activate the CIP cycle, and the delivery portion 330 runs independently of the insertion portion 310 with water. This cycle keeps running until the cavity 320 is cleaned, which can be confirmed by internal medication sensor, which does not detect water.

Figure 6:
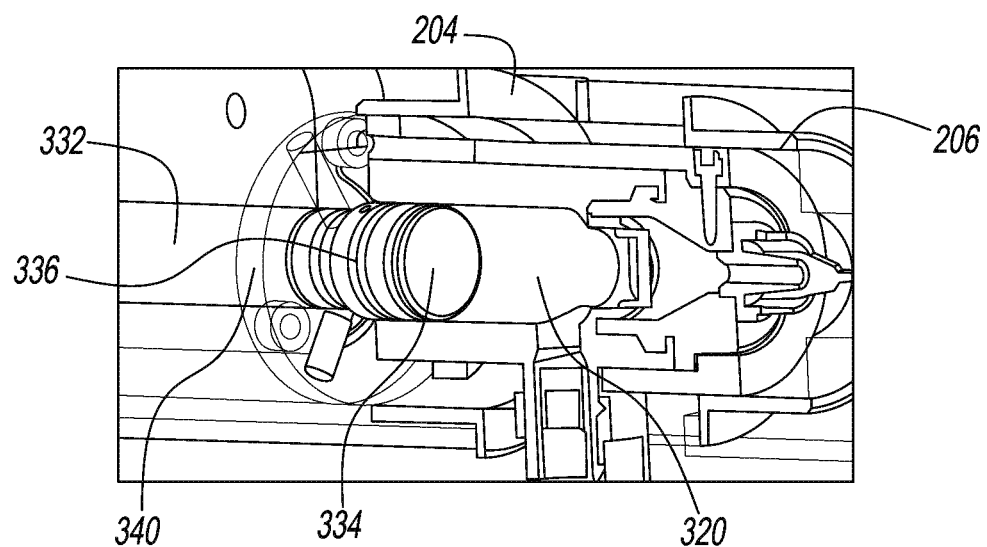
FIG. 6 illustrates an isometric view of the two stage insertion and delivery mechanism according to an exemplary embodiment.

FIG. 6 illustrates an isometric view of the insertion and delivery mechanism 200, with a cross section of the insertion portion 310.

The insertion and delivery mechanism 200 further includes a selectably actuable mechanism or trigger ring 340. The trigger ring 340 is connected to the insertion portion 310 by being fixed to the proximal portion of the syringe block 316 by fasteners 342. The trigger ring 340 is also connected to the rod 332 of the delivery portion 330. However, the trigger ring 340 attachment is not fixed, and the trigger ring 340 can be released from a specific position on the rod 332 and allow to the rod 332 to move independently of the trigger ring 340.

The trigger ring 340 may be in the shape of a ring, with a through hole, through which the rod 332 may fit. The through hole would have a similar cross section as the rod 332 to ease the passage of the rod through the through hole. The trigger ring 340 is within the first bearing 204, and within the proximal end of the first bearing 204.

Figure 7:
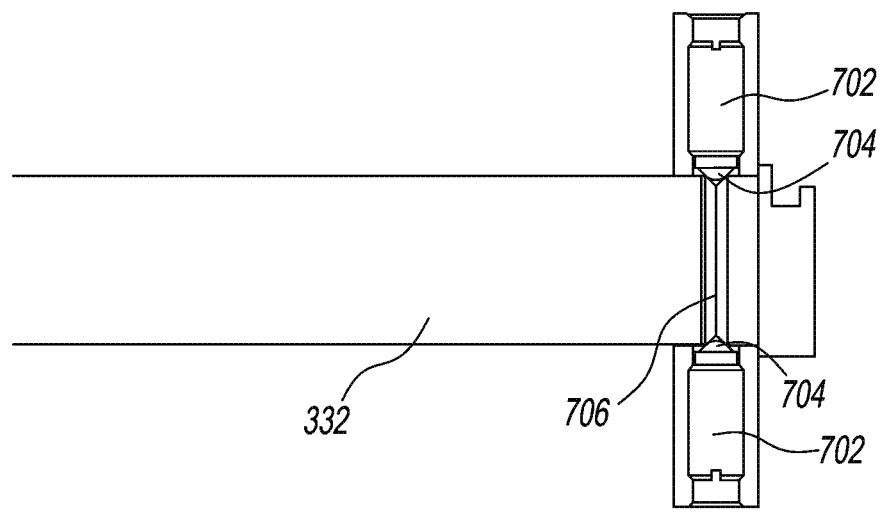
FIG. 7 illustrates a side view of a delivery portion with a trigger ring engaged with the delivery portion, according to one embodiment.

FIG. 7 illustrates a detailed side view an exemplary embodiment of the trigger ring 340. Within the trigger ring 340 are a plurality of bias mechanisms 702 that are radially spaced. There may be, for example, two to four bias mechanisms in the trigger ring 340. Each bias mechanism 702 has a ball bearing 704 that is in contact with the rod 332. Each bias mechanism 702 applies a constant predetermined amount of force on the rod 332.

Figure 8:
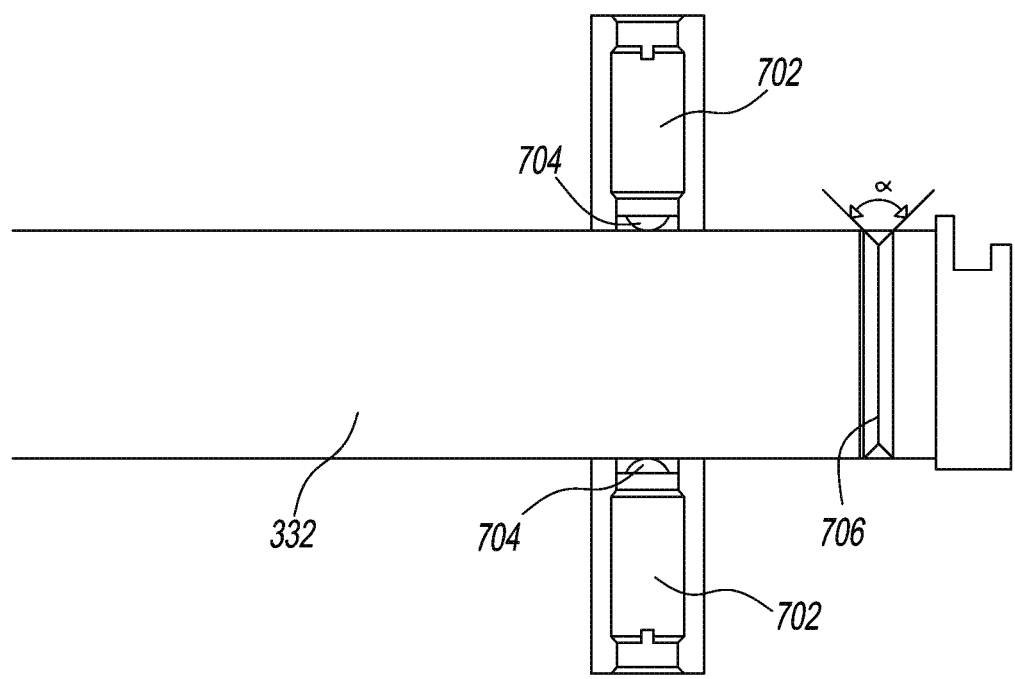
FIG. 8 illustrates a side view of a delivery portion with the trigger ring disengaged with the delivery portion, according to the embodiment of FIG. 7.

Near the distal end of the rod 332, there is a circumferential groove 706, with an angle "α". The angle "α" can be 90°±30°. The ball bearings 704 of each bias mechanism 702 are in the circumferential groove 706. The ball bearings 704 remain in the groove 706 until a predetermined amount of force is applied by the linear actuator 202 through the rod 332, and the ball bearings 704 slide out of the circumferential groove 706, and slide along the rod 332, as illustrated in FIG. 8.

In this manner, when the bias mechanisms 702 are in the circumferential groove 706, the delivery portion 330 and the insertion portion 310 move together. When the force increases to the predetermined threshold, the trigger ring 340 releases from the rod 332. The amount of force to release the trigger ring 340 from the rod 332 should be between the amount of force to insert the needle 106 into the animal and the amount of force to deliver the medication. For example, 12N±4N, which is between 5N and 65N. When the trigger ring 340 releases from the rod 332, the delivery portion 330 moves independently of the insertion portion 310, thus allowing the medication to be delivered to the animal.

After the medication has been delivered to the animal, the rod retracts back to its original position, and the bias mechanisms 702 go back into the circumferential groove 706, which allows the delivery portion 330 and the insertion portion 310 to move together back to an unactuated position.

Figure 9:
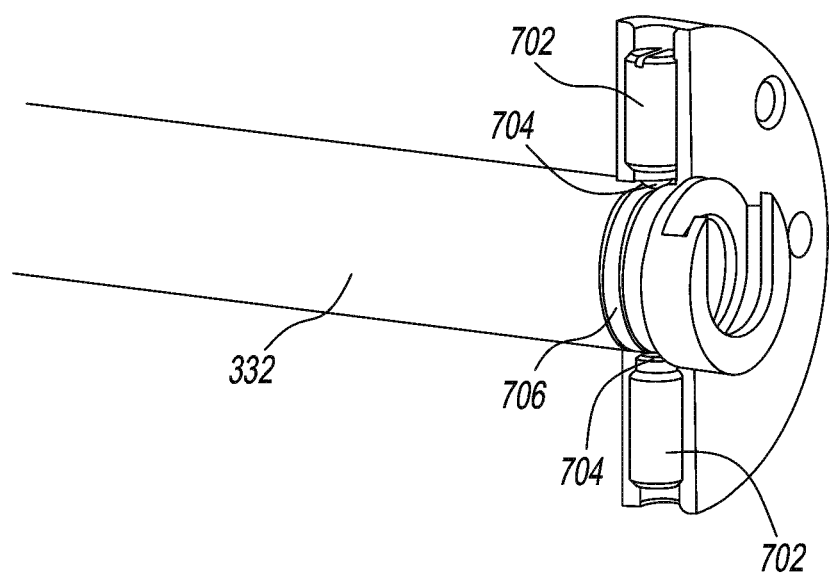
FIG. 9 illustrates an isometric view of a delivery portion with the trigger ring engaged with the delivery portion, according to the embodiment of FIG. 7.
Figure 10:
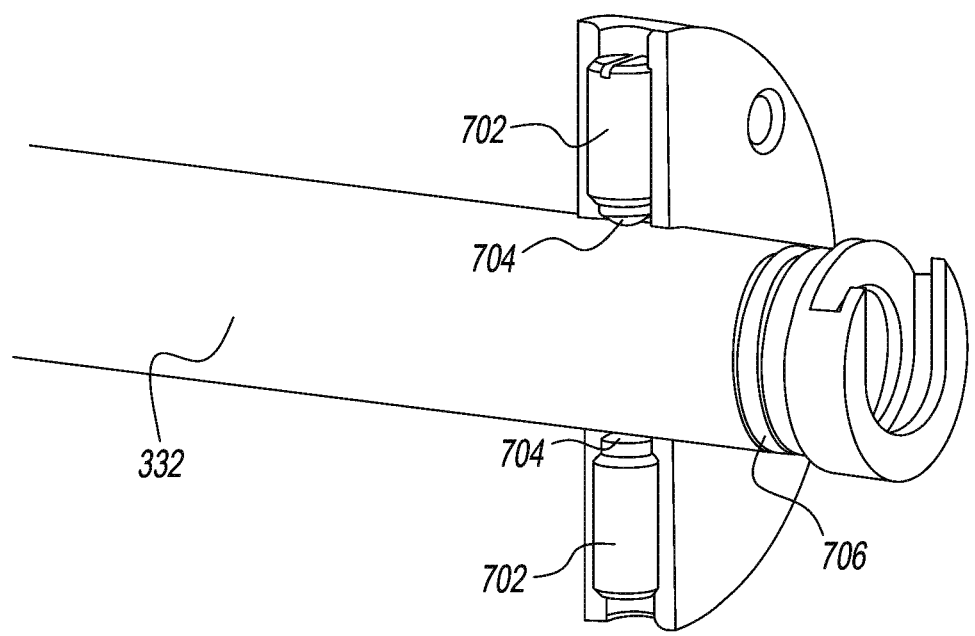
FIG. 10 illustrates an isometric of a delivery portion with the trigger ring disengaged with the delivery portion, according to the embodiment of FIG. 7.

FIGS. 9 and 10 illustrate an isometric view of the trigger ring 340. FIG. 9 illustrates when the bias mechanism 702 are in the circumferential groove 706 and FIG. 10 illustrates when the bias mechanisms 702 are not in the circumferential groove 706.

FIGS. 13-17 illustrate another embodiment of the applicator 100. The embodiment illustrated in FIGS. 13-17 have multiple similarities to the embodiment previously discussed and the similar references numbers are used to refer to similar components.

Figure 13:
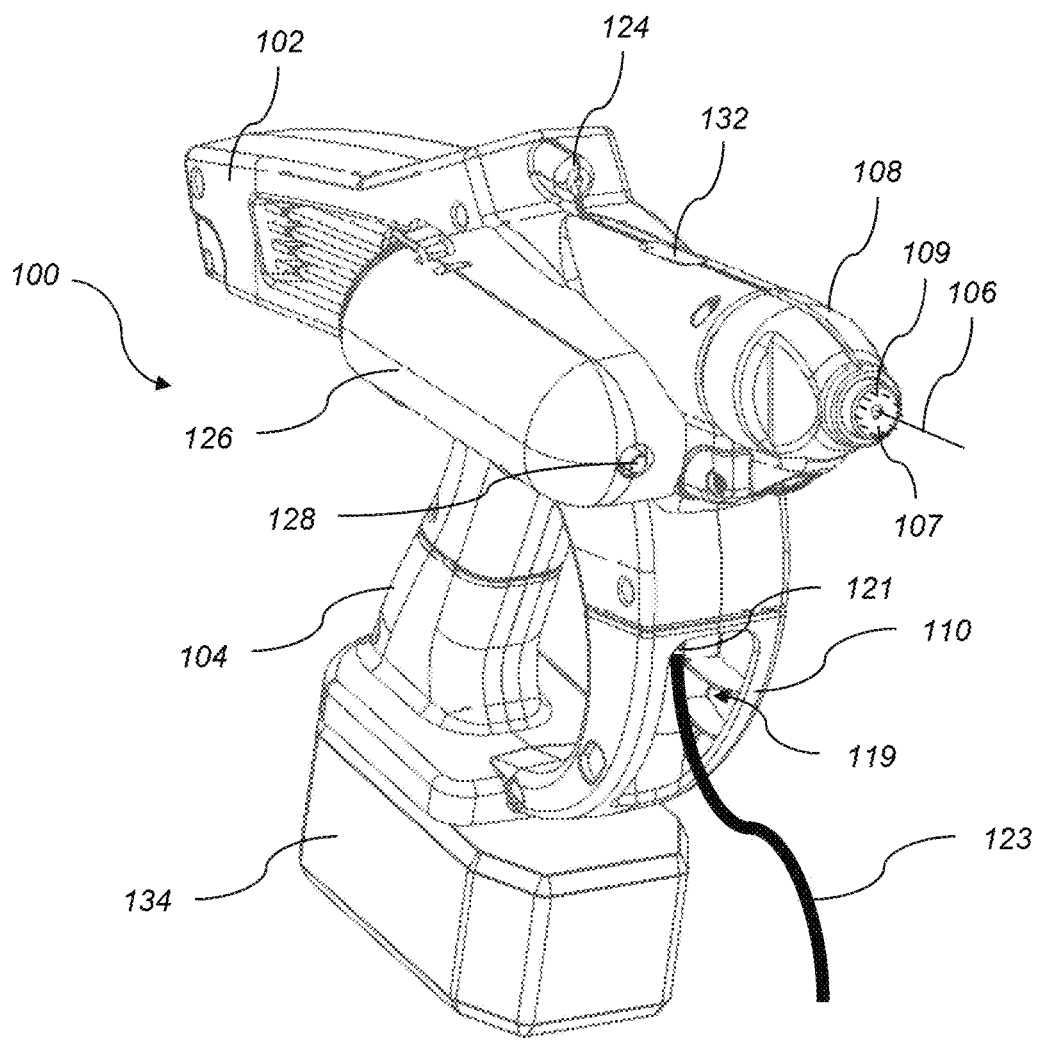
FIG. 13 illustrates an isometric view of an exemplary embodiment of an applicator.

FIG. 13 illustrates an isometric view of an applicator 100. The needle 106 of the applicator 100 is configured to extend out of the nose 108 of the applicator 100. As discussed previously, the needle 106 extends out of the applicator during injection and delivery of the medication, but otherwise is housed within the nose of the applicator 100. The needle 106 extends out of a flat portion 107 of the nose 108. The flat portion 107 also includes a plurality of grippers 109 that extend out of the flat portion 107 for a predetermined distance. The grippers 109 are arranged radially around the flat portion 107 and surround the needle 106, however alternative variations of the location of the grippers may be used. The grippers 109 stick into the animal and help secure the applicator 100 as the needle is inserted into the animal during the injection and delivery process, so that the applicator 100 does not slip during the vaccination process.

Figure 20:
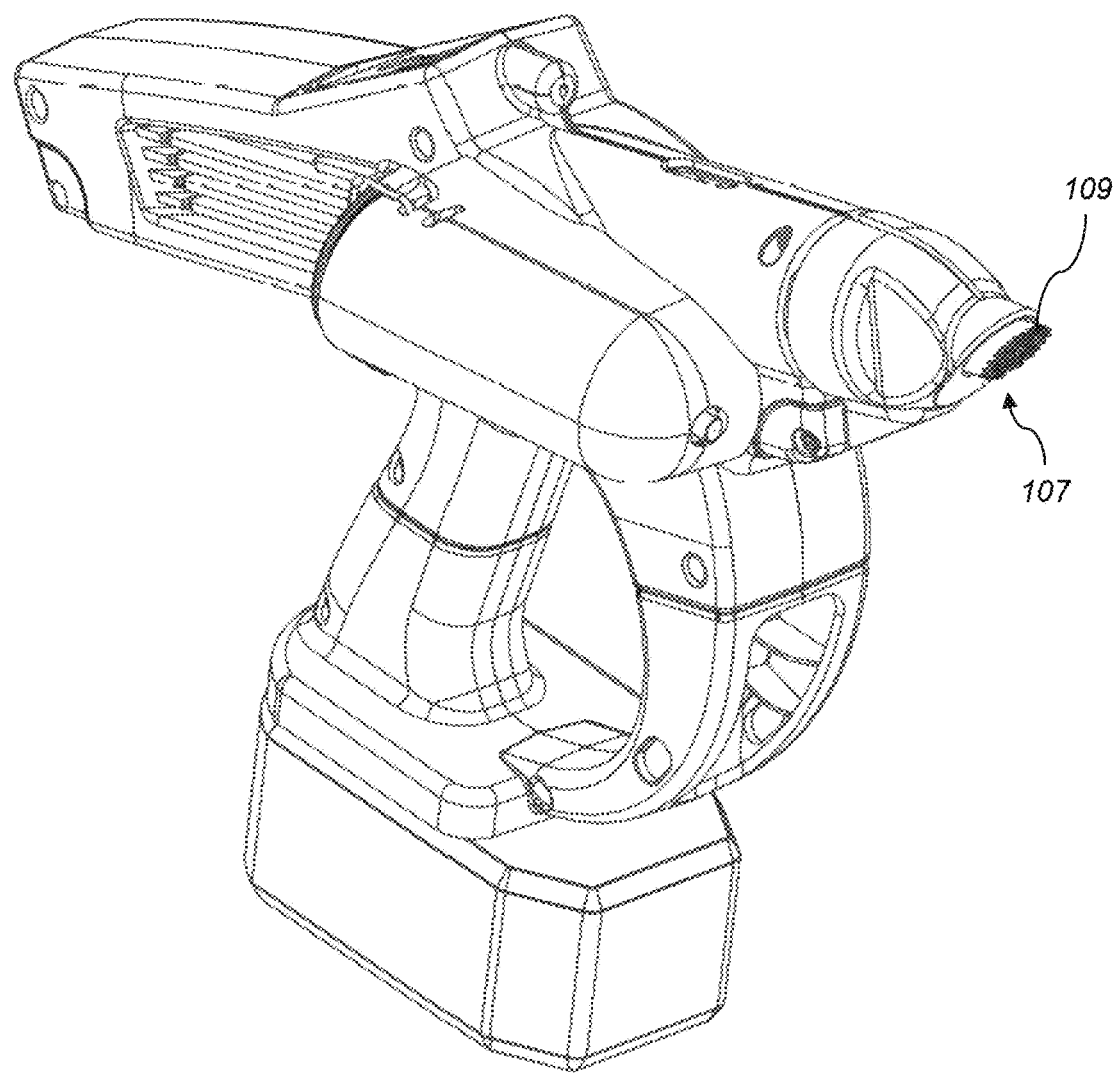
FIG. 20 illustrates an isometric view of an exemplary embodiment of an applicator.

Alternatively, the flat portion 107 of the nose 108 may have a different shape. For example, FIG. 20 illustrates the flat portion 107 may be angled so that the top portion of the flat portion 107 extends further than the bottom portion of the flat portion 107, but the angle between the top portion and the bottom portion is constant. The grippers 109 may be arranged radially around the flat portion 107 and surround the needle 106. Alternatively, as illustrated in FIG. 20, the grippers 109 may be arranged on the entirety of the flat portion 107. The angled flat portion 107 enables the applicator 100 to be applied more naturally to the skin of the animal.

In addition, the hand guard 110 illustrated in FIG. 13 has an opening 119 located on a front portion of the hand guard 110. The opening 119 exposes a connection 121 that is within the hand guard 110 to be exposed. This connection 121 is configured to be connected to tubing 123 and a medication bag (not shown). The medication in the medication bag is pumped from the bag, through the tubing 123 and into the cavity 320 through an inlet 322. The medication bag can contain a variety of substances, such as drugs, medicine, remedies, therapeutic preparations, vitamins, neutraceutricals, vaccines, antibodies, and the like.

FIG. 13 further illustrates an alternative embodiment for the guiding mechanism 124. The guiding mechanism 124 in FIG. 13 is located above the needle 106 and is located near the display 114. The guiding mechanism 124 may be a laser or LED which helps the user guide the applicator 100 to an appropriate location on the animal. The location of the guiding mechanism illustrated in FIG. 13 has an added benefit of a more accurate guiding beam. For example, as the user moves the applicator 100 toward the animal based on the guiding mechanism, the longer distance the light travels helps maintain the position of the light on the animal.

Figure 14:
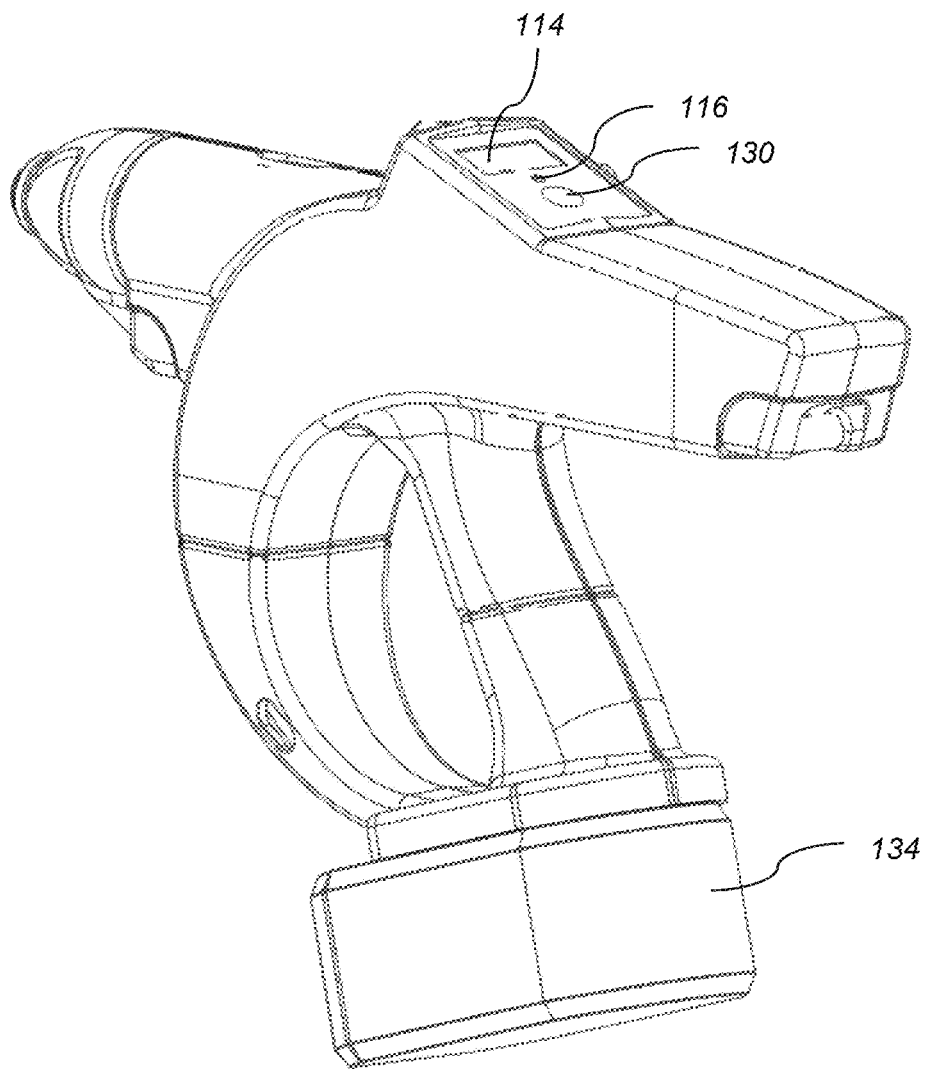
FIG. 14 illustrates an isometric view of an exemplary embodiment of the applicator as shown in FIG. 12.

FIG. 14 illustrates an alternative isometric view of the applicator 100. FIG. 14 illustrates the display 114, the LED 116, and the reset button 130.

Figure 15:
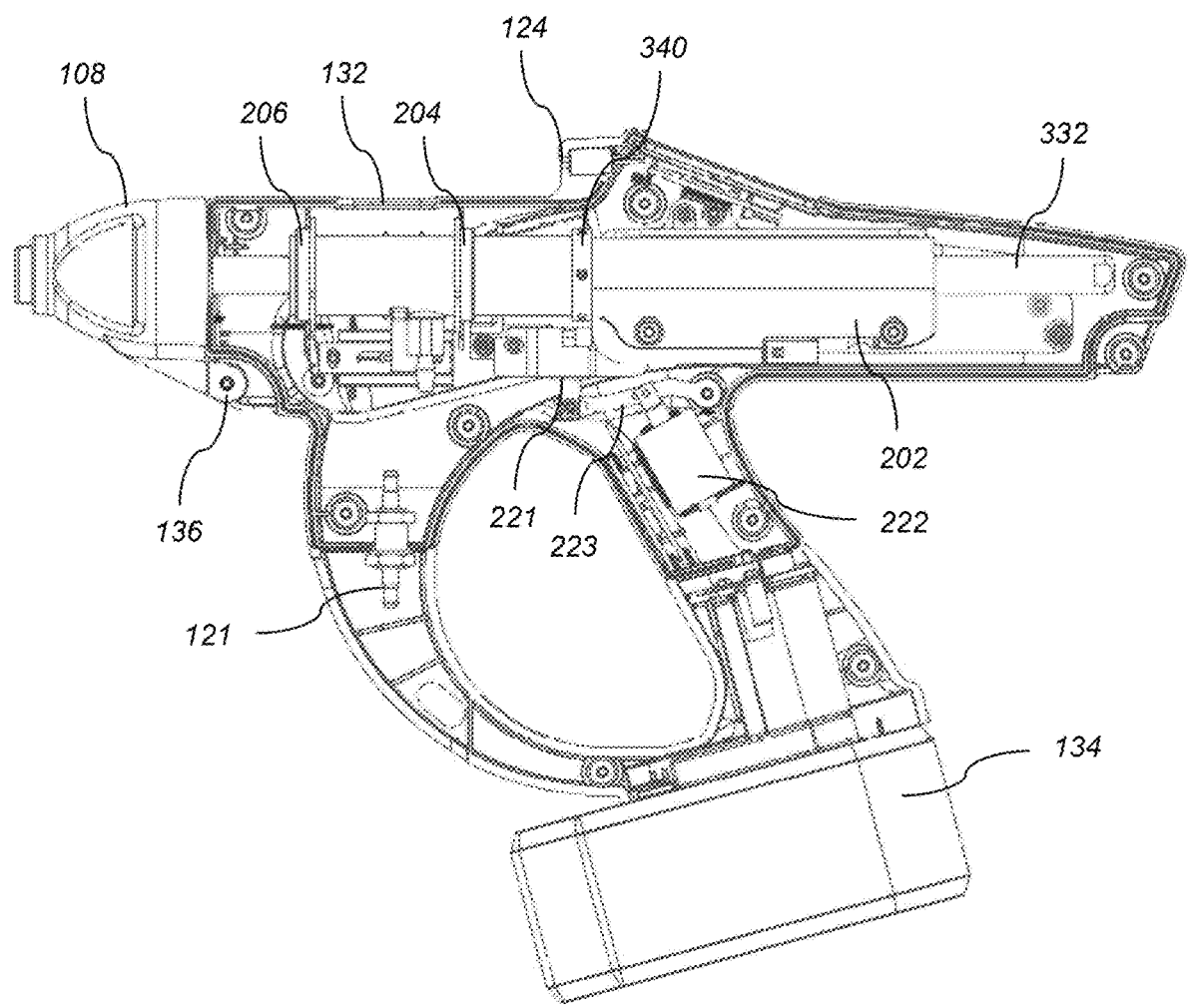
FIG. 15 illustrates an isometric cross-sectional view of an exemplary embodiment of the application as shown in FIG. 12.

FIG. 15 illustrates an isometric cross-sectional view of the applicator 100. The nose 108 is configured to open and close in order to allow easy exchange of the needle 106. For example, the nose 108 has a hinge 136 to allow the nose 108 to open and rotate about the hinge 136. The nose 108 of the applicator 100 may be secured by a number of different methods. For example, the nose 108 may be secured by nose magnets, with a magnet in the nose 108 and a corresponding magnet in the applicator housing 102 opposite the magnet in the nose 108. A predetermined amount of force is needed to separate the magnets and open the nose 108. When the nose 108 is opened, the current needle 106 can be unscrewed and replaced with a new needle 106.

Figure 16:
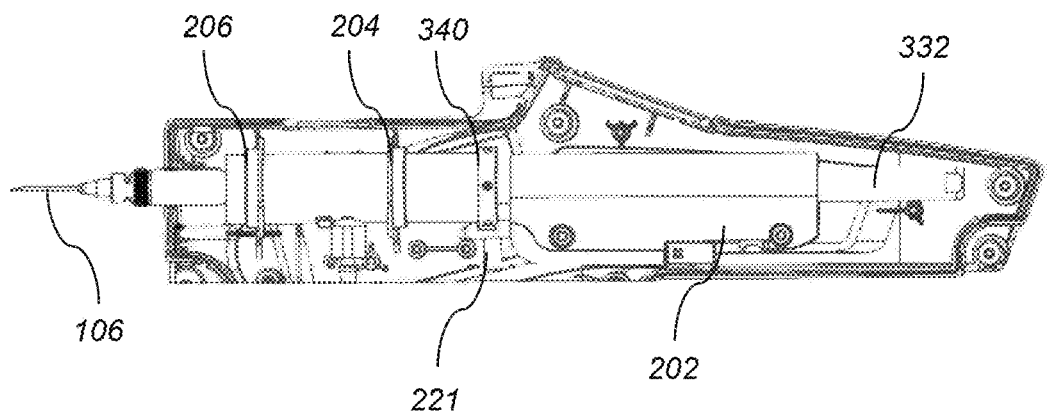
FIG. 16 illustrates a cross-sectional view of a two stage insertion and delivery mechanism and the latch according to the exemplary embodiment illustrated in FIG. 15.
Figure 17:
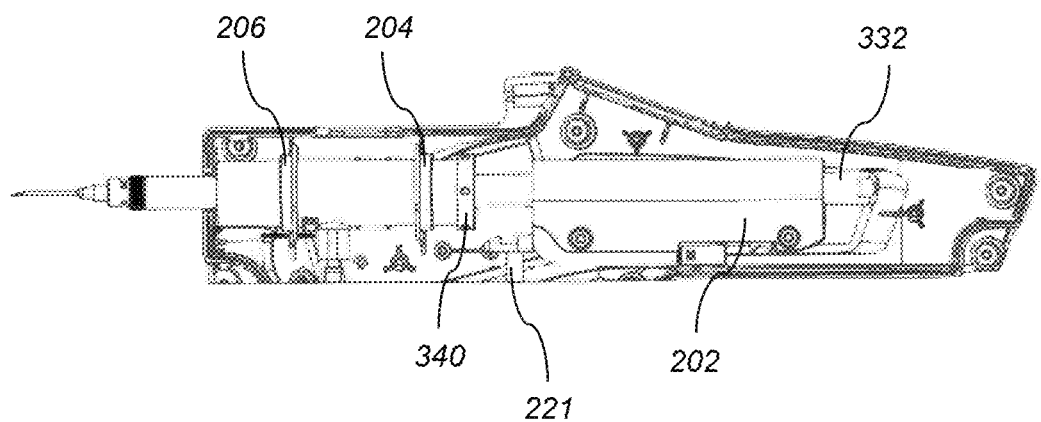
FIG. 17 illustrates a cross-sectional view of the two stage insertion and delivery mechanism and the latch according to the exemplary embodiment illustrated in FIG. 15.

FIG. 15 also illustrates the latch 221, which was previously disclosed. The latch 221 is also illustrated in FIGS. 16 and 17. The latch 221 locks the injection portion 310 of the applicator 100 in place and secures the triggering ring 340. When the triggering ring 340 is locked in place, the delivery portion 330 may move independently of the insertion portion 310. The latch 221 serves an additional security feature as the latch 221 keeps the needle 106 inside the nose 108 of the applicator 100 unless the applicator 100 is in the vaccination process. The latch 221 is moved by a connecting rod 223, and the connecting rod is moved by an electromagnet 222.

FIGS. 16 and 17 further illustrate the latch 221 in use. FIG. 16 illustrates the latch 221 in the default position. The latch 221 is maintained in the default position as an added security measure to ensure that the needle 106 does not extend out of the nose 108 (not shown in FIGS. 16 and 17) of the applicator 100 except for during the injection and delivery process in order to avoid accidental needle sticks. The latch 221 secures the triggering ring 340, which enables the rod 332 of the delivery portion 330 to move linearly and not move the needle 106. Priming the applicator 100 and the cleaning operation are performed when the latch 221 secures the triggering ring 340.

FIG. 17 illustrates when the latch 221 is released from the triggering ring 340. The electromagnet 222 pulls the connecting rod 223 to lower the latch 221 to release the latch 221 from the triggering ring 340. This action enables the applicator to perform the injection and delivery process. After the injection and delivery process is completed, the latch 221 returns to the default position in which the latch 221 secures the triggering ring 340. The processing circuitry controls the electromagnet 222 which controls position of the latch 221.

The processing circuitry within the applicator 100 controls the amount of force applied by the linear actuator 202. The amount of force applied by the linear actuator 202 may be determined by the linear distance traveled by the rod, time, etc.

Since the processing circuitry controls the amount of force applied by the linear actuator 202, the trigger ring 340 may act as a mechanical failsafe for the applicator 100, and prevent the rod 332 from moving independently until the predetermined amount of force is applied. The medication can only be delivered if the rod 332 and piston 334 move independent of the insertion portion 310, and the rod 332 and piston 334 can only move independent of the insertion portion 310 if the trigger ring 340 is released from the rod 332.

Figure 11A:
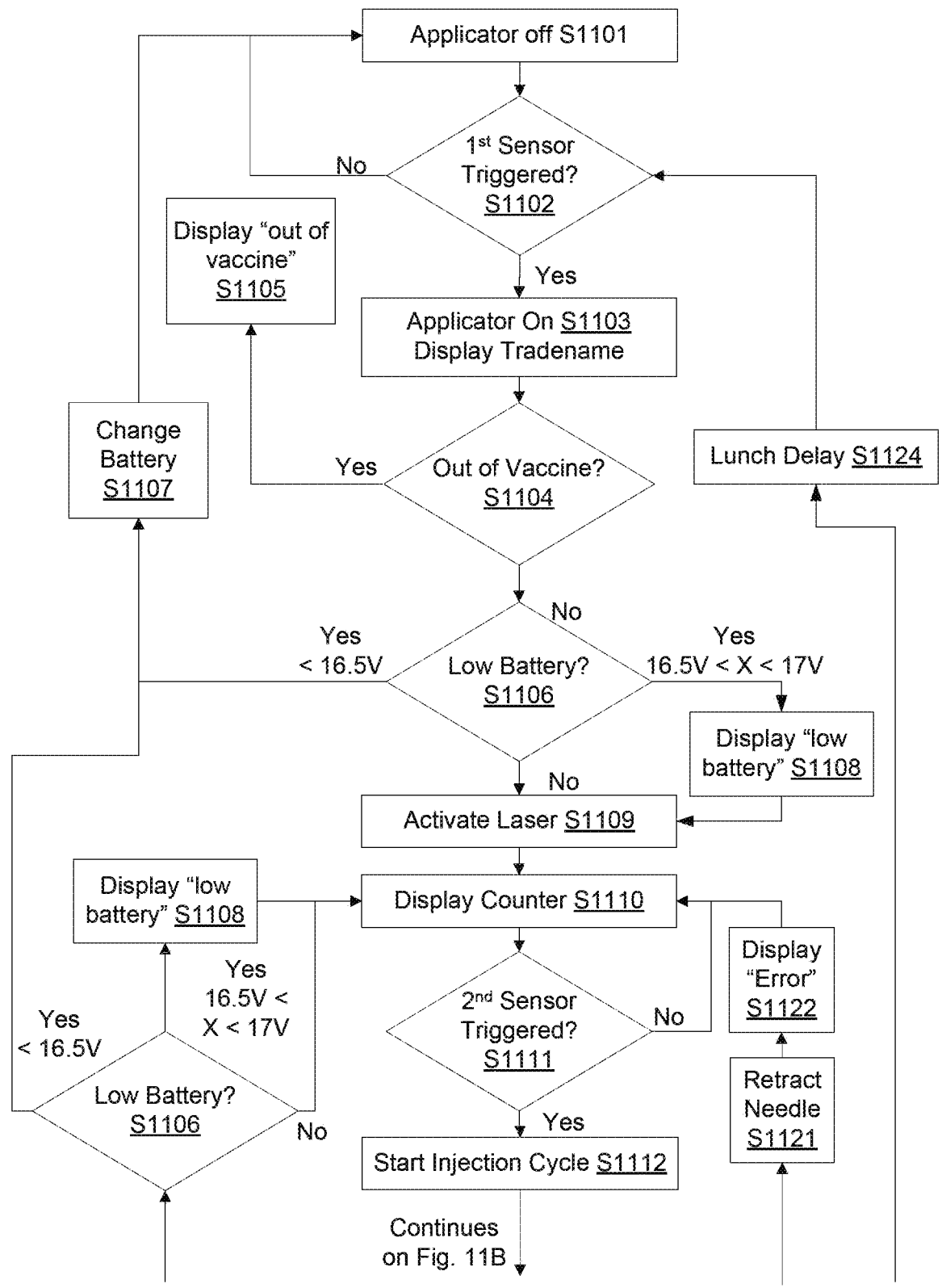
FIGS. 11A-11B illustrate a flowchart of the use of the applicator to inject a dose of medication to the animal.
Figure 11B:
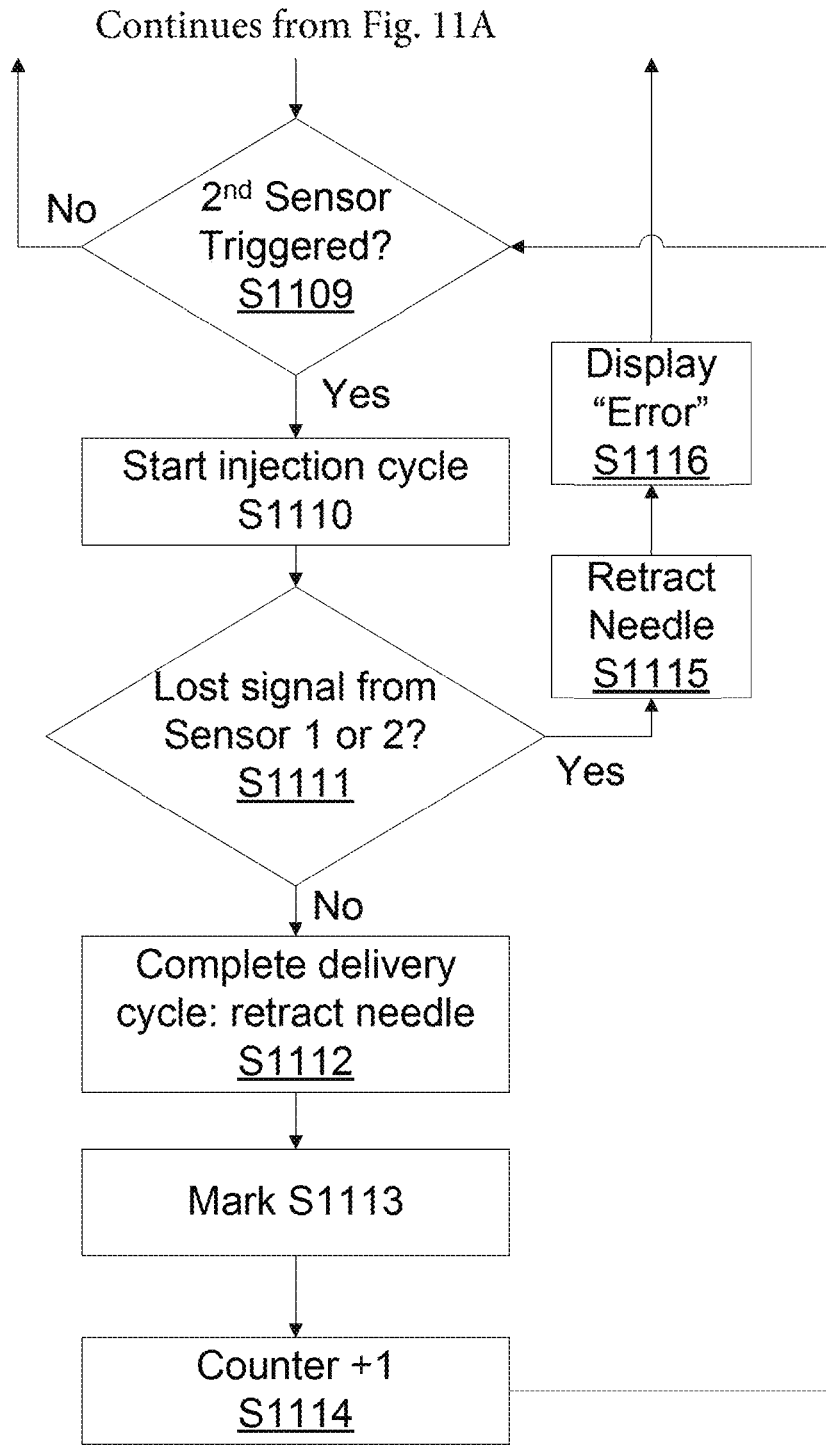

FIG. 11 illustrates a flowchart of how the processing circuitry acts in conjunction with the applicator 100 to insert the needle 106 into the animal and deliver a dose of medication.

In S1101, the applicator 100 is off. In S1102, the user triggers the first sensor 112, for example, the handle presence sensor, discussed earlier, to turn on S1103 the applicator 100. The first sensor 112 is triggered when it detects the presence of the user gripping the handle 104 of the applicator 100. When the user triggers the first sensor 112, a signal is sent from the first sensor 112 to the processing circuitry to turn on the applicator 100, S1103. When the applicator 100 turns on, the screen 114 and the light 116 turn on to indicate to the user that the applicator 100 is ready for use. When the screen 114 turns on, a trade name could be displayed on the screen 114 to the user.

The applicator can request various information from the user about the vaccination session that is about to commence. For example, for records purposes, the location can be inputted, such as the name of the farm, the specific barn or other location, the vaccine to be used etc. This information can be stored in the applicator to be later uploaded to a network, personal computer, laptop, mobile device, or the like.

However, if at any point, the first sensor signal is lost, the processing circuitry will begin to shut down and turn off the applicator 100. For example, after the applicator 100 turns on, if the signal to the processing circuitry from the first sensor is lost, or in other words, the first sensor 112 no longer detects the presence of the user gripping the handle 104, the processing circuitry turns off the applicator 100. According to one embodiment, the applicator 100 turns off immediately after the first sensor signal is lost. In the off mode, the applicator 100 waits for the first sensor 112 to be triggered to turn the applicator 100 back on. In this way, the applicator can conserve battery power when not in use.

Alternatively, according to one embodiment, the applicator 100 does not turn off immediately when the first sensor signal is lost. The applicator 100 can remain on for a predetermined amount of time before turning off. If the user does not grip the handle 104 within the predetermined amount of time, for example 60 seconds, the applicator 100 can turn off.

In S1104, the processing circuitry determines if there is any vaccine in the internal cavity 320. The internal medication sensor sends a signal to the processing circuitry to indicate when there is sufficient medication in the cavity 320. If there is not enough medication, the applicator 100 displays to the user that the applicator 100 is "out of vaccine" S1105. However, if there is sufficient medication, the processing circuitry continues.

In S1106, if the battery sensor detects if there is enough power in the battery to inject the animal. If there is not enough battery, the applicator 100 can give a change battery warning S1107 to the user to change the battery. For example, if the battery has a charge of less than 16.5 volts, the change battery warning 1107 is given. However, if the battery is low on power, but has enough power to do an injection cycle, the applicator can give a low battery warning S1108 to the user, and processing circuitry continues to the next step. For example, if the battery has a charge between 16.5 and 17 volts, a low battery warning is given to the user.

However, if there is enough battery to inject the animal and there is a dose of medication in the cavity 320, and the needle 106 has been primed, then the applicator 100 can begin the injection process. The user can be signaled that the applicator 100 is ready for use through the screen 114, the light 116, and the use of audio. Once the applicator 100 is ready for use, the laser 124 can be activated S1109 to signal to the user the applicator is 100 ready for injection. The user can use the laser 124 to position the applicator 100 and place the nose 108 of the applicator 100 in the appropriate location on the animal for the injection.

The applicator 100 can further include has a counter. The counter can keep track of the number of injections the applicator 100 has given. The counter can keep track of the number of injections for the lifetime of the applicator 100, and also the number of injections the current bottle of medication has given, etc. The count can be displayed on the screen 114. After the laser is activated S1109, the counter is displayed S1110 on the screen 114.

In S1111, the second sensor 118 can be triggered. The second sensor 118 can be the animal contact sensor 118, discussed earlier. The animal contact sensor can be triggered when the user places the nose 108 of the applicator 100 in contact with the skin of the animal. However, if the second sensor 118 is triggered before the first sensor 112, the applicator 100 will not do anything. The sensors need to be triggered in the proper order.

Once both sensors have been triggered and respective signals sent to the processing circuitry, the injection cycle begins. During the injection cycle, the processing circuitry sends a signal to the linear actuator 202 to apply a predetermined amount of force to extend the needle 106 out of the applicator 100 and insert the needle 106 into the animal. After the needle 106 has been inserted, the processing circuitry sends a signal to the linear actuator 202 to apply a second predetermined amount of force to deliver the medication through the needle 106 into the animal. After a successful insertion of the needle 106 and delivery of the medication, the needle 106 is retracted into the applicator 100 S1115 and another dose is loaded in cavity 320 for the next injection cycle. Only after the completion of a successful injection cycle, the processing circuitry signals for the applicator 100 to mark the animal with ink S1116.

After the animal has been marked in S1116, the counter adds another count to the counter S1117. The counter can play a part in the maintenance of the applicator 100. After a predetermined number of injections, the applicator can inform the user of needed maintenance. Different types of maintenance, or maintenance benchmarks, can be performed on the applicator 100 based on the number of injections given. For example, maintenance benchmarks could include: replacement of the needle, maintenance of the linear actuator 202, scheduled cleanings, part replacements, etc. For example, in S1118, if the total count is greater than 10,000, the applicator 100 displays a service "SRV" message S1119 to the user. However, if the count is less than 10,000, no message is displayed to the user.

The injection cycle can be repeated numerous times, as long as the user keeps his grip on the handle 104, there is sufficient medication, sufficient battery power, and the user places the applicator 100 against the skin of the next animal. In S1120, circuitry determines if the first sensor is still active. If the user is still holding the applicator 100 and activating the first sensor, the user can restart the injection process. Before the injection process begins again, the processing circuitry determines if there is any vaccine S1104 and if there if sufficient power in the battery S1106, as discussed previously. The processing circuitry waits for the second sensor to be triggered S1111 to start the injection cycle again S1112.

However, if the first sensor is lost after the injection cycle is complete and the counter has increased, and the animal marked, the processing circuitry will deactivate the laser S1123. After the laser S1123 is deactivated, the processing circuitry can launch a delay S1124. The delay is a process of postponing turning off if the user intends to continue to use the applicator. For example, if the user sets the applicator down between injections, the applicator can remain on for a predetermined amount of time before the applicator turns off.

However in S1113 and S1114, if at any point during the injection process, either signal is lost, meaning that one of the sensors is no longer triggered, then the injection cycle is aborted. For example, if the user took his hand off the handle 104 or the user took the nose 108 of the applicator 100 off the animal, the injection process would be terminated. In S1113 and S1114, the processing circuitry sends a signal to the linear actuator 202 to quickly retract the needle 106 into the applicator 100 S1119, and send an error message to the user S1120. The needle 106 is retracted quickly to prevent an accidental needle stick. The injection process can begin again after the first and second sensors have been triggered again in the proper order.

FIG. 11C further illustrates S1105. If the applicator 100 is out of vaccine, the user can insert a new vaccine bottle 122 into the applicator S1105(a). After the new vaccine bottle is inserted, the latch sensor S1105(c) determines if the latch is in place, in order to perform a prime. If the latch sensor S1105(c) indicates that the latch is in place, the user can press the reset button 130 or a command button to initiate the priming step S1105(d). After priming has been performed, the applicator is ready to being injection process.

After a vaccination session has been performed, any and all information collected during the session, such as operator name, location, farm name, types of animals injected, status of the sensors, number of successful and unsuccessful vaccinations, actuator temperature, the number of needle changes, temperature of the vaccine, vaccine batch numbers, and the like can be uploaded to a network, personal computer, laptop, mobile device or the like. This process can be performed through a Bluetooth module, Wifi, or any other wireless method. Alternatively, the applicator 100 may have a cord in order to communicate with another device directly.

The applicator 100 may further include an additional security system to prevent accidental needle sticks or accidental injections. The intended use of the applicator 100 is for a human to medicate animals of many different varieties. As discussed previously, accidental needle sticks and accidental injection are a real concern for the user. There are certain medications that are administered to animals that are severely hazardous to the user, for example, a castration vaccine. In order to avoid injecting the user with a hazardous medication, an additional security system may be used.

Figures 18A, 18B:
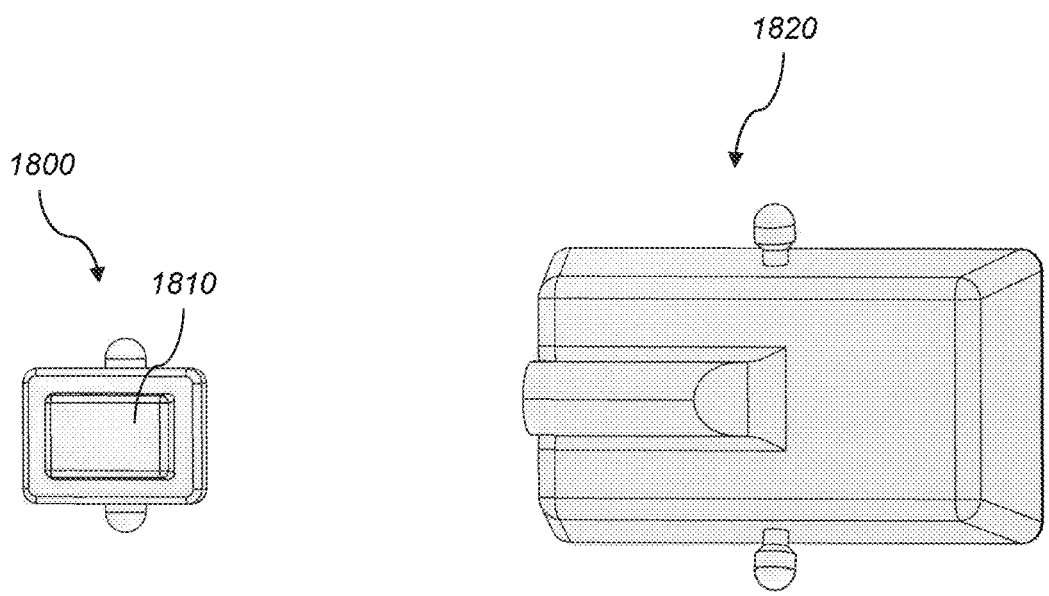
FIG. 18A illustrates a handheld component of an additional security system according to an exemplary embodiment.
FIG. 18B illustrates a second component of the additional security system according to an exemplary embodiment.

FIGS. 18A and 18B illustrate the additional security system, which includes two separate components. The first component is illustrated in FIG. 18A, which is a handheld component 1800. The handheld component 1800 includes a button 1810. The user holds the applicator 100 in one hand and holds the handheld component 1800 in the other hand. The user needs to press the button 1810 on the handheld component in order to activate the applicator 100. In other words, the applicator will not initiate the vaccination process unless the user has activated the button 1810 on the handheld component 1800.

FIG. 18B illustrates the second component 1820. The second component 1820 is attached to the user's wrist and is connected to the handheld component 1810. When the user activates the button on the handheld component, the second component transmits a signal to the applicator 100 by a transmitter to indicate that the user is ready to begin the injection cycle. The signal may be send by a wire or by other wireless methods, such as a radio frequency. The user needs to activate the button between each injection cycle. The applicator 100 has a receiver to receive the signal from the second component 1820 and the additional security feature is operated by the processing circuitry within the applicator 100.

Alternatively, the additional security system may be incorporated into a single device. For example, the handheld component 1800 may include the button 1810 and a transmitter to transmit the signal to the applicator 100.

Figure 19:
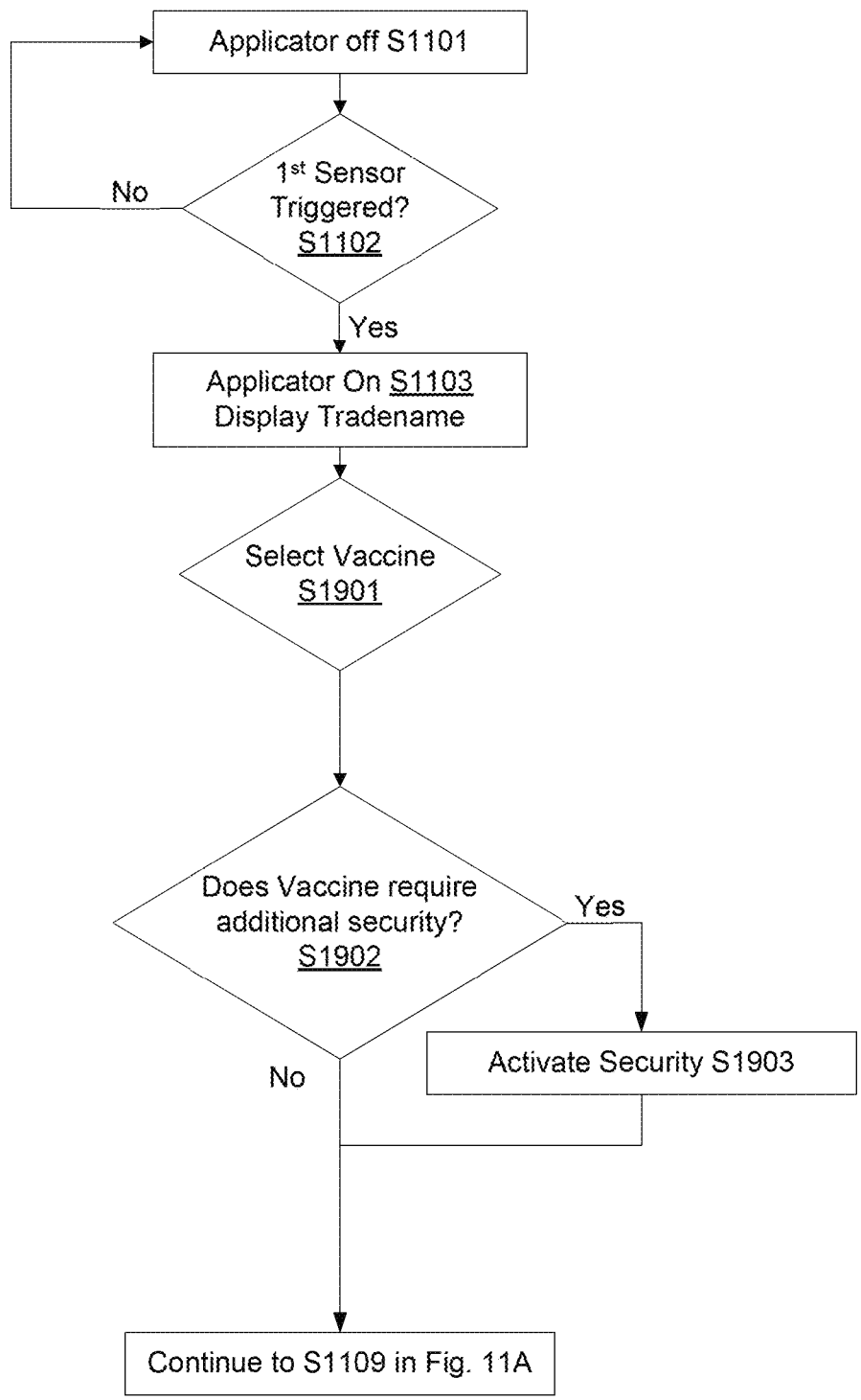
FIG. 19 illustrates a flowchart of the use of the applicator utilizing the additional security system.

FIG. 19 illustrates a flowchart of how the processing circuitry acts in conjunction with the applicator 100 and the additional security system. As discussed previously, the applicator is off until the user triggers the first sensor 112 in S1102. After the user activates the first sensor 112, a signal is sent from the first sensor 112 to the processing circuitry to turn on the applicator 100, S1103. When the applicator 100 turns on, the screen 114 and the light 116 turn on to indicate to the user that the applicator 100 is ready for use. When the screen 114 turns on, a trade name may be displayed on the display 114 to the user.

In S1901, the user selects the medication or vaccine to be used during that vaccination session. The display 114 may display the selected vaccine and request confirmation from the user that the proper medication or vaccine was selected. If the vaccine selected is deemed hazardous to the user, such as a castration vaccine, the additional security system is activated in S1903. However, if the vaccine selected has not been determined to be hazardous, the vaccination process can continue as outlined in FIG. 11A at S1109. The list of vaccines that are deemed hazardous can be controlled by the manufacture, the user, etc. For example, the additional security system could be used for all vaccines to ensure safety or simply for vaccines that have been determined by the user or manufacturer to be hazardous.

In S1903, the additional security system is activated and the vaccine cannot be administered unless the user activates the button 1810 on the handheld component 1800 between each vaccination cycle. When the user activates the button 1810 on the handheld component 1800 the second component transmits a signal to the applicator 100 to enable the vaccination cycle to proceed.

Figure 12:
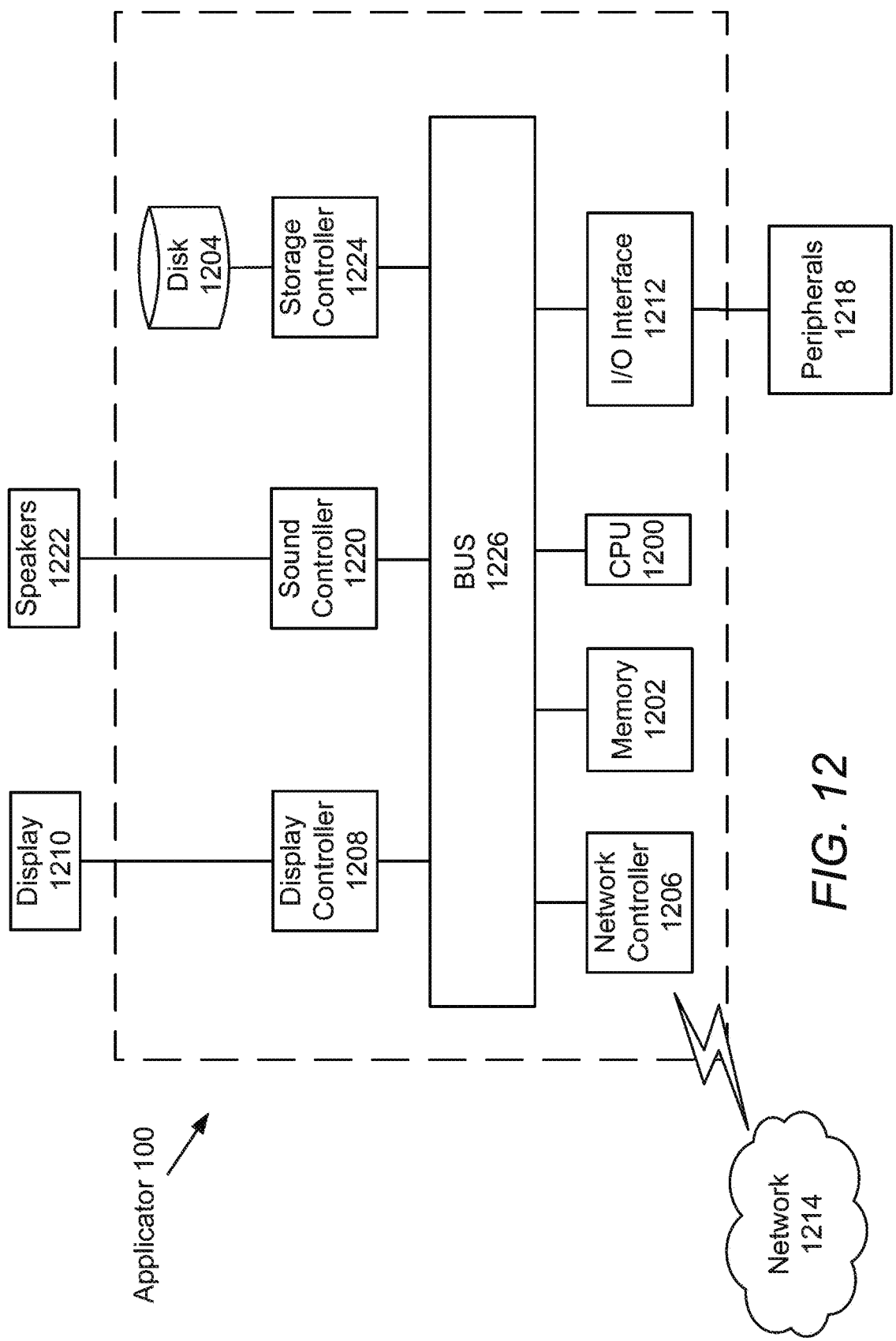
FIG. 12 illustrates a hardware device configuration of the applicator according to one example.

Next, a hardware description of the applicator 100 according to exemplary embodiments is described with reference to FIG. 12. In FIG. 12, the applicator 100 includes a CPU 1200 which can perform the processes described above. For example, the CPU 1200 can receive the signals from the sensors and control the activation of the linear actuator 202 through the insertion and delivery for the applicator 100. The process data and instructions may be stored in memory 1202. These processes and instructions may also be stored on a storage medium disk 1204 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the applicator 100 communicates, such as a server or computer.

Further, the claimed advancements may be provided as a utility application, background daemon, or component of an operating system, or combination thereof, executing in conjunction with CPU 1200 and an operating system such as Microsoft Windows, UNIX, Solaris, LINUX, Apple MAC-OS and other systems known to those skilled in the art.

CPU 1200 can be processing circuitry, such as a Xenon or Core processor from Intel of America or an Opteron processor from AMD of America, or may be other processor types that would be recognized by one of ordinary skill in the art. Alternatively, the CPU 1200 or processing circuitry may be implemented on an field programmable gate array ("FPGA"), application-specific integrated circuit ("ASIC"), programmable logic device ("PLD") or using discrete logic circuits, as one of ordinary skill in the art would recognize. Further, CPU 1200 may be implemented as multiple processors cooperatively working in parallel to perform the instructions of the inventive processes described above.

The applicator 100 in FIG. 12 also includes a network controller 1206, such as an Intel Ethernet PRO network interface card from Intel Corporation of America, for interfacing with network 1214. As can be appreciated, the network 1214 can be a public network, such as the Internet, or a private network such as an LAN or WAN network, or any combination thereof and can also include PSTN or ISDN sub-networks. The network 1214 can also be wired, such as an Ethernet network, or can be wireless such as a cellular network including EDGE, 3G and 4G wireless cellular systems. The wireless network can also be WiFi, Bluetooth, or any other wireless form of communication that is known.

The applicator 100 further includes a display controller 1208, such as a NVIDIA GeForce GTX or Quadro graphics adaptor from NVIDIA Corporation of America for interfacing with display 1208, such as the screen 114. General purpose I/O interface also connects to a variety of peripherals 1218 including printers and scanners, such as an OfficeJet or DeskJet from Hewlett Packard.

A sound controller 1220 is also provided in the applicator, such as Sound Blaster X-Fi Titanium from Creative, to interface with speakers/microphone 1222 thereby providing sounds and/or music.

The general purpose storage controller 1224 connects the storage medium disk 1204 with communication bus 1226, which may be an ISA, EISA, VESA, PCI, or similar, for interconnecting all of the components of the applicator 100. A description of the general features and functionality of the display 114, the display controller 1208, storage controller 1224, network controller 1206, sound controller 1220, and general purpose I/O interface 1212 is omitted herein for brevity as these features are known.

Obviously, numerous modifications and variations of the present invention are possible in light of the above teachings. It is therefore to be understood that within the scope of the appended claims, the invention may be practiced otherwise than as specifically described herein.

What is claimed is:

1. A handheld injection safety applicator comprising:
an applicator housing;
a handle;
a retractable needle housed within the applicator;
a first sensor configured to detect the presence of a user's grip on the handle;
a second sensor configured to detect the presence of an animal;
a processing circuitry configured to
receive a first signal from the first sensor indicating that the user is gripping the handle;
receive a second signal from the second sensor indicating that an animal is detected;
extend the needle out of the applicator into the animal once the first and second signals are received; and
deliver a dose of medication into the animal once the needle is fully extended into the animal,
wherein the processing circuitry extends the needle by actuating a linear actuator with a first predetermined amount of force, and
wherein the processing circuitry actuates the linear actuator to deliver a dose of medication, after the needle has been extended, with a second predetermined amount of force that is greater than the first predetermine amount of force.

2. The handheld injection safety applicator of claim 1, wherein the processing circuitry controls the amount of force applied by a linear actuator, the amount of force being based on the linear distance a rod of the linear actuator has traveled inside the applicator.

3. The handheld injection safety applicator of claim 1, further comprising a two stage insertion and delivery mechanism within the applicator housing that includes an insertion portion that includes the retractable needle, a cavity that is within the insertion portion which houses the dose of medication, and a delivery portion that moves within the cavity.

4. The handheld injection safety applicator of claim 3, wherein the extension of the retractable needle by the processing circuitry causes a linear actuator to apply the first predetermined amount of force, which causes the insertion portion and the delivery portion to move together relative to the applicator housing a predetermined amount of distance.

5. The handheld injection safety applicator of claim 4, wherein the delivery of the medication by the processing circuitry causes the linear actuator to apply the second predetermined amount of force, which allows the delivery portion to move independently of the insertion portion and within the cavity and deliver the dose of medication through the retractable needle into the animal.

6. The handheld injection safety applicator of claim 5, further including a selectably actuable mechanism, the selectably actuable mechism being fixed to the insertion portion, and releasably connected to the delivery portion, wherein the delivery portion is released from the selectably actuable mechanism when a force greater than or equal to a third predetermined force is applied by the linear actuator, the third predetermined force being between the first and second predetermined amount of force.

7. The handheld injection safety applicator of claim 1, the applicator further includes an ink marker that actuates ink through an orifice, the orifice being directed toward the animal during the insertion and delivery process, wherein the processing circuitry only actuates ink through the orifice to mark the animal after a complete dose has been delivered to the animal.

8. The handheld injection safety applicator of claim 1, wherein the applicator delivers a 2 ml dose of medication to the animal.

9. The handheld injection safety applicator of claim 1, wherein the first predetermined amount of force is between 4 to 6 N.

10. The handheld injection safety applicator of claim 1, wherein the second predetermined amount of force is between 60 and 70 N.

11. An injection safety applicator comprising:
an applicator housing; and
a two stage insertion and delivery mechanism within the applicator housing that includes an insertion portion, a cavity, a delivery portion and a selectably actuatable mechanism, the selectably actuable mechanism arranged to sequentially engage the delivery portion so that the insertion portion and the delivery portion move together relative to the applicator housing when the two stage insertion and delivery mechanism is actuated with a first force that is less than or equal to a predetermined force threshold, and then disengage the delivery portion to allow the delivery portion to move within the cavity independently of the insertion portion when the two stage insertion and delivery mechanism is actuated with a second force that is greater than the predetermined threshold force.

12. A method of injecting and delivering a dose of medication, the method comprising the steps of:

sensing a user holding a handle of a handheld applicator, which triggers a first sensor in the handle to indicate that the applicator is being held by the user;

receiving a first signal from the first sensor that the user is holding the applicator;

sensing the user applying the applicator to the skin of an animal to be injected, which triggers a second sensor in the applicator to indicate that an animal is ready to be injected;

receiving a second signal from the second sensor that the user is applying the applicator to the skin of the animal;

inserting a retractable needle into the animal only after receiving the first and second signals from the first and second sensors; and delivering a dose of medication through the retractable needle into the animal only after the needle has been inserted into the animal, wherein a first predetermined amount of force required to insert the retractable needle into the animal and a second predetermined amount of force needed to deliver the dose is provided by applicator and not the user, and the second predetermined amount of force is greater than the first predetermined amount of force.

13. The method of claim 12, wherein the inserting the retractable needle includes moving a two stage insertion and delivery mechanism within the applicator housing that includes an insertion portion that includes the retractable needle, a cavity that is within the insertion portion which houses the dose of medication, and a delivery portion that moves within the cavity, wherein the delivering the does medication includes moving the delivery portion independently of the insertion portion and within the cavity to deliver the dose of medication through the retractable needle into the animal, wherein the handheld applicator includes a selectably actuable mechanism including a trigger ring fixed to the insertion portion and releasably connected to the delivery portion, the trigger ring includes biasing mechanisms that are radially spaced around the trigger ring, each of the biasing mechanism including a ball bearing that is positioned in a circumferential groove of the delivery portion, and wherein the delivery portion is released from the selectably actuable mechanism when a force greater than or equal to a third predetermined force is applied by the linear actuator to remove the ball bearings from the circumferential groove, the third predetermined force being between the first and second predetermined amount of force.

14. The handheld injection safety applicator of claim 5, further comprising a selectably actuable mechanism that includes a trigger ring fixed to the insertion portion and releasably connected to the delivery portion, the trigger ring including biasing mechanisms that are radially spaced around the trigger ring, each of the biasing mechanism including a ball bearing that is positioned in a circumferential groove of the delivery portion wherein the delivery portion is released from the selectably actuable mechanism when a force greater than or equal to a third predetermined force is applied by the linear actuator to remove the ball bearings from the circumferential groove, the third predetermined force being between the first and second predetermined amount of force.

15. The injection safety applicator of claim 11, wherein the selectably actuable mechanism includes biasing mechanisms arranged radially around a trigger ring to sequentially engage the delivery portion via ball bearings of the biasing mechanisms being positioned in a circumferential ring of the deliver portion so that the insertion portion and the delivery portion move together relative to the applicator housing when the two stage insertion and delivery mechanism is actuated with the first force that is less than or equal to the predetermined force threshold, and then disengage the delivery portion by removing the ball bearings from the circumferential ring to allow the delivery portion to move within the cavity independently of the insertion portion when the two stage insertion and delivery mechanism is actuated with the second force that is greater than the predetermined threshold force.

* * * * *